Figure 1A:
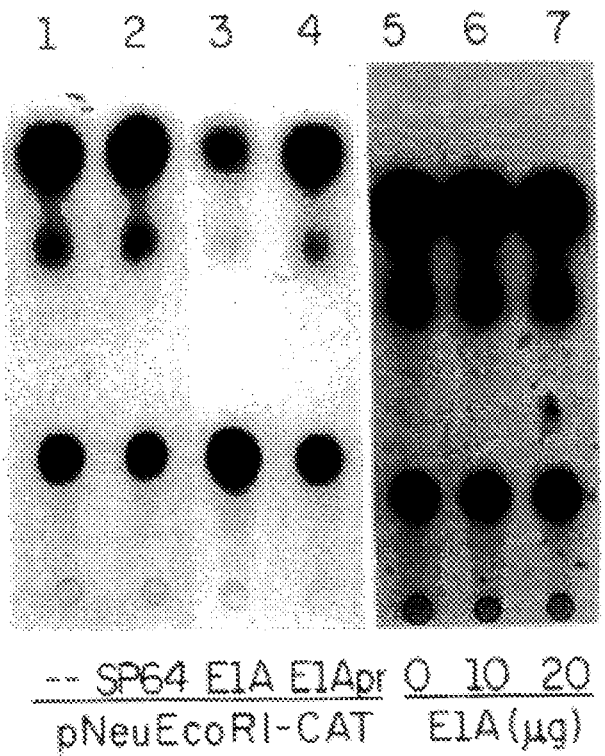

United States Patent [19]

Hung et al.

[11] Patent Number: 5,651,964

[45] Date of Patent: *Jul. 29, 1997

[54] METHODS FOR THE SUPPRESSION OF NEU MEDIATED TUMORS BY THE ADENOVIRAL E1A GENE

[75] Inventors: Mien-Chie Hung; Di-Hua Yu, both of Houston, Tex.

[73] Assignee: Board of Regents, The University of Texas System, Austin, Tex.

[*] Notice: The term of this patent shall not extend beyond the expiration date of Pat. No. 5,643,567.

[21] Appl. No.: 70,410

[22] PCT Filed: Dec. 4, 1991

[86] PCT No.: PCT/US91/09100

§ 371 Date: Jun. 4, 1993

§ 102(e) Date: Jun. 4, 1993

Related U.S. Application Data

[63] Continuation-in-part of Ser. No. 621,465, Dec. 4, 1990, abandoned.

[51] Int. Cl.$^6$ .............. A61K 48/00; A01N 63/00; C12N 15/00

[52] U.S. Cl. .............. 424/93.2; 424/93.6; 435/320.1; 935/55; 935/56; 935/57

[58] Field of Search .............. 514/44; 424/93 B, 424/93.2, 93.6; 435/172.3, 320.1; 935/62, 55, 56, 57

[56] References Cited

U.S. PATENT DOCUMENTS 4,394,448  7/1983  Szoka, Jr. et al. .............. 435/172

FOREIGN PATENT DOCUMENTS

WO 90/15595  12/1990  WIPO .
WO 93/03769   3/1993  WIPO .
WO 94/21115   9/1994  WIPO .

OTHER PUBLICATIONS

Vausden et al (1989) Oneogene 4, 153–158.

Shin (1979) Meth. Enzymol. 58, 370–379.

Yu et al., "Transcriptional Repression of the neu Protooncogene by the Adenovirus 5 E1A Gene Products," *Proc. Natl. Acad. Sci. USA*, 87:4499–4503, 1990.

Teramota et al., "Serum Enzyme Immunoassay Kit for the Detection of c–erbB–2 Oncoprotein," Annual AACI Meeting, Abstract #1446, 1991j.

Zhang et al., "Amplification and Rearrangement of c–erb B Proto–Oncogenes in Cancer of Human Female Genital Tract," *Oncogene*, 4:985–989, 1989.

Slamon et al., "Studies of the HER–2/neu Proto–Oncogene in Human Breast and Ovarian Cancer," *Science*, 244:707–712, 1989.

Steeg et al., "Altered Expression of NM23, a Gene Associated with Low Tumor Metastatic Potential, during Adenovirus 2 E1a Inhibition of Experimental Metastasis," *Cancer Res.*, 48:6550–6554, 1988.

Smith & Ziff, "The Amino–Terminal Region of the Adenovirus Serotype 5 E1a Protein Performs Two Separate Functions when Expressed in Primary Baby Rat Kidney Cells," *Mol. Cell Biol.*, 8(9):3882–3890, 1988.

Bargmann & Weinberg, "Increased Tyrosine Kinase Activity Associated with the Protein Encoded by the Activated neu Oncogene," *Proc. Natl. Acad. Sci. USA*, 85:5394–5398, 1988.

Pozzatti et al., "The E1a Gene of Adenovirus Type 2 Reduces the Metastatic Potential of ras–Transformed Rat Embryo Cells," *Mol. Cell Biol.*, 8(7):2984–2988, 1988.

Whyte et al., "Two Regions of the Adenovirus Early Region 1A Proteins Are Required for Transformation," *J. Virol.*, 62(1):257–265, 1988.

Egan et al., "Transformation by Oncogenes Encoding Protein Kinases Induces the Metastatic Phenotype," *Science*, 238:202–205, 1987.

Sassone–Corsi & Borrelli, "Promoter Trans–Activation of Protooncogenes c–fos and c–myc, but not c–Ha–ras, by Products of Adenovirus Early Region 1A," *Proc. Natl. Acad. Sci. USA*, 84:6430–6433, 1987.

Kraus et al., "Overexpression of the EGF Receptor–Related Proto–Oncogene erbB–2 in Human Mammary Tumor Cell Lines by Different Molecular Mechanisms, "*EMBO J.*, 6(3): 605–610, 1987.

Slamon et al., "Human Breast Cancer: Correlation of Relapse and Survival with Amplification of the HER–2/neu Oncogene," *Science*, 235:177–182, 1987.

Pozzatti et al., "Primary Rat Embryo Cells Transformed by One or Two Oncogenes Show Different Metastatic Potentials," *Science*, 232:223–227, 1986j.

Stern et al., "p185, a Product of the neu Proto–Oncogene, Is a Receptorlike Protein Associated with Tyrosine Kinase Activity," *Mol. Cell Biol.*, 6(5):1729–1740, 1986.

Schecter et al., "The neu Gene: An erbB–Homologous Gene Distinct from and Unlinked to the Gene Encoding the EGF Receptor," *Science*, 229:976–978, 1985.

Brunet et al., "Concentration Dependence of Transcriptional Transactivation in Inducible E1A–Containing Human Cells," *Mol. Cell. Bio.*, 8(11):4799–4807 (1988).

(List continued on next page.)

*Primary Examiner*—Deborah Crouch
*Attorney, Agent, or Firm*—Arnold, White & Durkee

[57] ABSTRACT

Disclosed are methods and compositions for the suppression of expression of the neu oncogene, as well as suppression of neu oncogene-mediated transformation, tumorigenesis and metastasis. The method disclosed involved introduction of adenovirus early 1A gene (the E1A gene) products into affected cells. These products, which are preferably introduced by transfection of the E1A gene into affected cells, serve to suppress neu gene expression as measured by a reduction of p185 expression. Furthermore, the E1A gene products surprisingly serve to suppress the oncogenic phenotype, as indicated by a reduction in cell growth, growth in soft agar, as well as tumorigenic and metastatic potential in vivo. The inventors propose that E1A gene products, or derivatives therefrom, may ultimately be employed a treatment modalities for neu-mediated cancers, such as cancers of the female genital tract and breast.

8 Claims, 16 Drawing Sheets

OTHER PUBLICATIONS

Felgner et al., "Gene Therapeutics: The Direct Delivery of Purified Genes in vivo and Their Application as Drugs, Without the Use of Retroviruses, Is Discussed," *Nature*, 349:351–352 (1991).

Frisch et al., "Adenovirus E1A Represses Protease Expression and Inhibits Metastasis of Human Tumor Cells," *Oncogene*, 5:75–83 (1990).

Harlow et al., "Monoclonal Antibodies Specific for Adenovirus Early Region 1A Proteins: Extensive Heterogeneity in Early Region 1A Products," *J. of Virology*, 55(3):533–546 (1985).

Hearing et al., "Sequence–Independent Autoregulation of the Adenovirus Type 5 E1A Transcription Unit," *Mol. Cell. Bio.*, 5(11):3214–3221 (1985).

Nabel et al., "Site–Specific Gene Expression in Vivo by Direct Gene Transfer into the Arterial Wall," *Science*, 249:1285–88 (1990).

Moran et al., "Multiple Functional Domains in the Adenovirus E1A Gene," *Cell*, 48:177–178 (1987).

Ruley, "Adenovirus Early Region 1A Enables Viral and Cellular Transforming Genes to Transform Primary Cells in Culture," *Nature*, 304:602–606 (1983).

Senear et al., "Morphological Transformation of Established Rodent Cell Lines by High–Level Expression of the Adenovirus Type 2 E1a Gene," *Mol. Cell. Bio.*, 6(4):1253–1260 (1986).

Suen et al., *Breast Cancer Research and Treatment*, 14(1):Abstract 213 (1989).

Whyte et al., "Association between an Oncogene and an Anti–Oncogene: The Adenovirus E1A Proteins Bind to the Retinoblastoma Gene Product," *Nature*, 334:124–129 (1988).

Yu et al., "Adenovirus Type 5 E1A Gene Products Act as Transformation Suppressors of the neu Oncogene," *Mol. Cell. Bio.*, 11(3): 1745–1750 (1991).

Yu, et al., Manuscript–"Enhanced c–erbB–2/neu Expression in Human Ovarian Cancer Cells Correlates with More Severe Malignancy That Can Be Suppressed by E1A" (1992).

Zhou, et al., "A Retrovirus Vector which Transduces a Functional Estrogen Receptor Gene at High Efficiency," *Mol. Endocrinology*, 3(7):1157–1164 (1989).

Zhou, et al., *Chemical Abstracts*, 14(21): 205–Abstract No. 114:200732Z (1991).

Bargmann et al., "Multiple Independent Activations of the neu Oncogene by a Point Mutation Altering the Transmembrane Domain of p185," *Cell*, 45:649–657, 1986.

Bargmann et al., "The neu Oncogene Encodes an Epidermal Growth Factor Receptor–Related Protein," *Nature*, 319:226–230, 1986.

Berk and Sharp, "Structure of the Adenovirus 2 Early mRNAs," *Cell*, 14:695–711, 1978.

Fung et al., "Activation of the Cellular Oncogene c–erbB by LTR Insertion: Molecular Basis for Induction of Erythroblastosis by Avian Leukosis Virus," *Cell*, 33:357–368, 1983.

Berk, "Adenovirus Promoters and E1A Transactivation," *Ann. Rev. Genet.*, 20:45–79, 1986.

Coussens et al., "Tyrosine Kinase Receptor with Extensive Homology to EGF Receptor Shares Chromosomal Location with neu Oncogene," *Science*, 230:1132–1139, 1985.

Downward et al., "Close Similarity of Epidermal Growth Factor Receptor and v–erb–B Oncogene Protein Sequences," *Nature*, 307:521–527, 1984.

Haley et al., "Transformation Properties of Type 5 Adenovirus Mutants that Differentially Express the E1A Gene Products," *Proc. Natl. Acad. Sci. USA*, 81:5734–5738, 1984.

Houweling et al., "Partial Transformation of Primary Rat Cells by the Leftmost 4.5% Fragment of Adenovirus 5 DNA," *J. Virology*, 105:537–550, 1980.

Hung et al., "Amplification of the Proto–neu Oncogene Facilitates Oncogenic Activation by a Single Point Mutation, " *Proc. Natl. Acad. Sci. USA*, 86:2545–2548, 1989.

Hung, "The neu Proto–Oncogene and Breast Cancer, " *Cancer Bull.*, 40:300–303, 1988.

Hung et al., "Molecular Cloning of the neu Gene: Absence of Gross Structural Alteration in Oncogenic Alleles, " *Proc. Natl. Acad. Sci. USA*, 83:261–264, 1986.

Land et al., "Cellular Oncogenes and Multistep Carcinogenesis," *Science*, 222:771–776, 1983.

Lupu et al., "Direct Interaction of a Ligand for the erbB2 Oncogene Product with the EGF Receptor and p185$^{erbB2}$, " *Science*, 249:1552–1554, 1990.

Müller et al., "Differential Expression of Cellular Oncogenes During Pre–and Postnatal Development of the Mouse," *Nature*, 299:640–644, 1982.

Schechter et al., "The neu Oncogene: An erb–B–Related Gene Encoding a 185,000–$M_r$ Tumour Antigen," *Nature*, 312:513–516, 1984.

Semba et al., "A v–erbB–Related Protooncogene, c–erbB–2, Is Distinct from the c–erbB–1/Epidermal Growth Factor––Receptor Gene and Is Amplified in a Human Salivary Gland Adenocarcinoma," *Proc. Natl. Acad. Sci. USA*, 82:6497–6501, 1985.

Shih et al., "Transforming Genes of Carcinomas and Neuroblastomas Introduced into Mouse Fibroblasts," *Nature* 290:261–264, 1981.

Wallich et al., "Abrogation of Metastatic Properties of Tumour Cells by de novo Expression of H–2k Antigens Following H–2 Gene Transfection," *Nature*, 315:301–305, 1985.

Yamamoto et al., "Similarity of Protein Encoded by the Human c–erb–B–2 Gene to Epidermal Growth Factor Receptor," *Nature*, 319:230–232, 1986.

Yarden and Weinberg, "Experimental Approaches to Hypothetical Hormones: Detection of a Candidate Ligand of the neu Protooncogene," *Proc. Natl. Acad. Sci. USA*, 86:3179–3183, 1989.

Douglas et al., "Modulation of transformation of primary epithelial cells by the second exon of the Ad5 E1A12S gene," *Oncogene*, 6:2093–2103, 1991.

Montell et al., "Complete Transformation by Adenovirus 2 Requires Both E1A Proteins," *Cell*, 36:951–961, 1984.

Offringa et al., "A Novel Function of the Transforming Domain of E1a: Repression of AP–1 Activity," *Cell*, 62:527–538, 1990.

Whyte et al., "Cellular Targets for Transformation by the Adenovirus E1A Proteins," *Cell*, 56:67–75, 1989.

Freedman and Shin, "Use of Nude Mice for Studies on the Tumorigenicity of Animal Cells, " *The Nude Mouse in Experimental and Clinical Research*, 1978.

Gazit et al., "Chemo-adoptive immunotherapy of nude nice implanted with human colorectal carcinoma and melanoma cell lines," *Cancer Immunology Immunotherapy*, 35:135–144, 1992.

Inoue, et al., "Consideration of Simultaneous Combination Chemotherapy— Employing a Sensitivity Test in Dunn Osteosarcoma and NR Fibrosarcoma by Intra–Test Tube Contact of Tumor Cell Suspension, and Subcutaneous Inoculation–," *J. Jpn. Soc. Cancer Ther.* 25(12):2781–2789, 1989.

Hung et al., "Transcriptional repression of the HER 2/ucu protooncogene by transforming oncogenes from DNA tumor virus," *Proceedings of the American Association for Cancer Research*, vol. 31, Mar. 1990.

0 20 15 10 5
E1A (μg)

0 20 15 10 5
E1A-13S (μg)

0 20 15 10 5
E1A-12S (μg)

0 20 15 10 5
E1Adl346 (μg)

Tumorigenicity assay

| Cell Line | Time to develope tumors (No. of tumors/no. of injection) | | | | | | Tumor volume at 16 days (mm³) |
|---|---|---|---|---|---|---|---|
| | 8 | 12 | 14 | 20 | 26 (days) | | |
| B104-1-1 | 6/6 | 6/6 | 6/6 | 6/6 | 6/6 | | 8240±203 |
| NIH3T3 | 0/6 | 0/6 | 0/6 | 0/6 | 0/6 | | N.D. |
| N-E1A-1 | 0/6 | 0/6 | 0/6 | 0/6 | 0/6 | | N.D. |
| B-E1A-1 | 0/6 | 0/6 | 0/6 | 5/6 | 6/6 | | N.D. |
| B-E1A-2 | 0/6 | 2/6 | 6/6 | 6/6 | 6/6 | | 216±53 |
| B-E1A-3 | 0/6 | 6/6 | 6/6 | 6/6 | 6/6 | | 481±74 |

FIG. 9A

METHODS FOR THE SUPPRESSION OF NEU MEDIATED TUMORS BY THE ADENOVIRAL EIA GENE

This is a continuation-in-part of application U.S. Ser. No. 07/621,465, filed Dec. 4, 1990, now abandoned.

The government has rights to this invention pursuant to NIH Grant No. CA-45265.

The present invention relates to methodology and associated genetic constructs for the suppression of oncogene-mediated, transformation, tumorigenesis and metastasis. In particular, this invention relates to the suppression of oncogenesis that is mediated by the HER-2/c-erb B-2/neu oncogene, an oncogene which has been correlated with a poor prognosis of breast and ovarian carcinoma in humans.

During the last decade, scientists have discovered that the occurrence of a number of human malignancies can be correlated with the presence and expression of "oncogenes" in the human genome. More than twenty different oncogenes have now been implicated in tumorigenesis, and are thought to play a direct role in human cancer (Weinberg, R. A., 1985). Many of these oncogenes apparently evolve through mutagenesis of a normal cellular counterpart, termed a "proto-oncogene", which leads to either an altered expression or activity of the expression product. There in, in fact, much data linking proto-oncogenes to cell growth, including their expression in response to certain proliferation signals (see, e.g., Campisi et al., 1983) and expression during embryonic development (Muller et al., 1982). Moreover, a number of the proto-oncogenes are related to either a growth factor or a growth factor receptor.

The c-erbB gene encodes the epidermal growth factor receptor (EGFr) and is highly homologous to the transforming gene of the avian erythroblastosis virus (Downward et al., 1984) The c-erbB gene is a member of the tyrosine-specific protein kinase family to which many proto-oncogenes belong. The c-erbB gene has recently been found to be similar, but distinct from, an oncogene referred to variously as c-erbB-2, HER-2 or neu oncogene (referred to herein simply as the neu oncogene), now known to be intimately involved in the pathogenesis of cancers of the human female breast and genital tract.

The neu oncogene, which encodes a p185 tumor antigen, was first identified in transfection studies in which NIH 3T3 cells were transfected with DNA from chemically induced rat neuroglioblastomas (Shih et al., 1981). The p185 protein has an extracellular, transmembrane, and intracellular domain, and therefore has a structure consistent with that of a growth factor receptor (Schechter et al., 1984). The human neu gene was first isolated due to its homology with v-erbB and EGF-r probes (Sebba et al., 1985).

Molecular cloning of the transforming neu oncogene and its normal cellular counterpart, the neu proto-oncogene, indicated that activation of the neu oncogene was due to a single point mutation resulting from one amino acid change in the transmembrane domain of the neu encoded p185 protein (Bargmann et al., 1986; Hung et al., 1989).

The neu oncogene is of particular importance to medical science because its presence is correlated with the incidence of cancers of the human breast and female genital tract. Moreover, amplification/overexpression of this gene has been directly correlated with relapse and survival in human breast cancer (Slamon et al., 1987). Therefore, it is an extremely important goal of medical science to evolve information regarding the neu oncogene, particularly information that could be applied to reversing or suppressing the oncogenic progression that seems to be elicited by the presence or activation of this gene. Unfortunately, little has been previously known about the manner in which one may proceed to suppress the oncogenic phenotype associated with the presence of oncogenes such as the neu oncogene.

An extensive body of research exists to support the involvement of a multistep process in the conversion of normal cells to the tumorigenic phenotype (see, e.g., Land et al., 1983). Molecular models supporting this hypothesis were first provided by studies on two DNA tumor viruses, adenovirus and polyomavirus. In the case of adenovirus, it was found that transformation of primary cells required the expression of both the early region 1A (E1A) and 1B (E1B) genes (Houweling et al., 1980). It was later found that the E1A gene products could cooperate with middle T antigen or with activate H-ras gene to transform primary cells (Ruley, H. E., 1985). These observations suggested that the involvement of multiple functions in the transformation process, and that various oncogenes may express similar functions on a cellular level.

The adenovirus E1A gene codes for several related proteins to which a number of interesting properties have been attributed. In addition to its ability to complement a second oncogene in transformation, a closely related function allows E1A to immortalize primary cells (Ruley, H. E., 1985). For example, introduction of E1A gene products into primary cells has been shown to provide these cells with an unlimited proliferative capacity when cultured in the presence of serum.

Another interesting action of E1A function is so-called "trans-activation", wherein E1A gene products stimulate transcription from a variety of viral and cellular promoters, including the adenovirus early and major late promoter. However, trans-activation is not universal for all promoters. In some instances, E1A causes a decrease in transcription from cellular promoters that are linked to enhancer elements (Haley et al., 1984). Recently, it has been shown that exogenously added E1A gene can reduce the metastatic potential of ras-transformed rat embryo fibroblast cells by activating the cellular NM23 gene that is associated with a lower metastatic potential (Pozzatti et al., 1988; Wallich et al., 1985).

The E1A gene products are referred to as the 13S and 12S products, in reference to the sedimentation value of two mRNAs produced by the gene. These two mRNAs arise through differential splicing of a common precursor, and code for related proteins of 289 and 243 amino acids, respectively. The proteins differ internally by 46 amino acids that are unique to the 13S protein. A number of E1A protein species can be resolved by PAGE analysis, and presumably arise as a result of extensive postranslational modification of the primary translation products (Harlow et al., 1985).

The present invention relates to the inventors' surprising discovery that, in contrast to the previous characterization of the E1A gene as being involved in promoting transformation, the E1A gene products can actually serve to suppress not only the expression of the neu oncogene, but suppress the oncogenic phenotype which accompanies neu oncogene activation. It is proposed that this exciting discovery opens the door to novel approaches to the treatment of neu oncogene-mediated cancers, as well as an improved understanding of the regulation of this oncogene in particular and the oncogenic phenotype in general.

The present invention thus arises out of the inventors' surprising discovery that products of the adenovirus E1A gene, a gene that is itself known to serve as an oncogene, can be effectively employed to suppress the transforming capability of the neu oncogene. Accordingly, the invention can be characterized in a general sense as relating to a method of suppressing neu oncogene-mediated transformation of a cell, which method includes introducing an E1A gene product into such a cell in a manner that is effective to suppress an oncogenic phenotype, as indicated by a reduction in transforming, tumorigenic or metastatic potential of the cell.

In general, in that it is proposed that the E1A gene products are directly responsible for the observed suppression of the oncogenic phenotype, it is believed that the objects of the invention may be achieved by introduction of E1A gene products intracellularly in any convenient manner, including, for example, virus mediated gene transfer, DNA transfection and even direct introduction of gene products by microinjection. It is proposed that methods such as these will work adequately, e.g., where one is seeking to study neu oncogene suppression. However, where a treatment regimen is contemplated it will likely be necessary to introduce the selected E1A gene product by intracellular introduction of a DNA segment which encodes the particular domain of the E1A protein that is required for repression of neu.

In any event, since the E1A gene products have been extensively characterized, and the gene itself has been cloned (see, e.g., Berk et al., 1978), the starting materials, i.e., the E1A products and gene, are readily available to those of skill in the art who desire to practice the invention. Where the gene itself is employed to introduce the gene products, the most convenient method of introduction will be through the use of a recombinant vector which incorporates the E1A gene, together with its associated control sequences. While use of the E1A control sequences (i.e., the E1A promoter) will be preferred, there is no reason why other control sequences could not be employed, so long as they are compatible with the genotype of the cell being treated. Thus, one may mention other useful promoters by way of example, including, e.g., an SV40 early promoter, a long terminal repeat promoter from retrovirus, an actin promoter, a heat shock promoter, a metallothianein promoter, and the like.

For introduction of the E1A gene, it is proposed that one will desire to preferably employ a vector construct that will deliver the E1A gene to the affected cells. This will, of course, generally require that the construct be delivered either to breast or genital tract cells. It is proposed that this may be achieved most preferably by introduction of the E1A gene through the use of a viral vector to carry E1A sequences to efficiently infect the tumor, or pretumorous tissue. These vectors will more preferably be a retrovital or vaccinia viral vector. These vectors are preferred because they have been successfully used to deliver desired sequences to cells and tend to have a high infection efficiency. Moreover, other virus vectors such as adenovirus have much larger genomes than vaccinia or retroviruses and are therefore undesirable for this reason.

A particularly desirable vector, at least as a starting point, is the E1A containing retroviral vector, termed pSVXE1A-G, described by Robert et al., 1985. This vector comprises the E1A gene which has been brought under the control of the SV-40 early promoter. The inventors propose that this construct could either be used directly in the practice of the invention, or could be used as a starting point for the introduction of other more desirable promoters such as those discussed above.

In that the inventors' studies have demonstrated that both the 12S and 13S E1A gene products are capable of suppressing neu gene expression, it is proposed that one may employ either product interchangeably, or both together, in the practice of the invention. Of course, in that the 12S and 13S products are derived from essentially the same gene sequences, and are merely the result of differential splicing, where the E1A gene itself is employed it will be most convenient to simply use the wild type E1A gene directly. However, it is contemplated that certain regions of the E1A gene may be employed exclusively without employing the entire wild type E1A gene. It is proposed that it will ultimately be preferable to employ the smallest region needed to suppress the neu gene so that one is not introducing unnecessary DNA into cells which receive the E1A gene construct.

In general, techniques for assessing the reduction in transforming, tumorigenic or metastatic potential are well known in the art. For example, the simplest assay is to measure the level of DNA synthesis in treated versus non-treated cells, in that DNA synthesis is a good measure of cell growth potential. Furthermore, the ability of transformed cells as compared to non-transformed cells to grow in soft agar has been widely employed as a measure of the transformation. Thus, either of these two assay techniques may be conveniently employed to assess the ability of the E1A products employed to suppress neu oncogene mediated transformation.

A number of accepted assays are also available where one desires to assess suppression of neu oncogene-mediated tumorigenic or metastatic potential. The most convenient indicator of tumorigenic potential, and indeed the most reliable, is an in vivo assay employing nude mice, wherein the ability of treated cells to cause tumors in the mice is assessed. Nude mice may be similarly employed where one desires to assess metastatic potential, by determining the ability of treated cells to form metastatic nodules, for example, in the lungs of experimental mice.

In that the inventors have observed that E1A gene products function through direct suppression of neu gene expression, the invention further concerns a method for suppressing neu gene expression or overexpression. In these embodiments, the method includes introducing an E1A gene product into the affected cell in a manner effective to suppress the cellular level of the neu p185 transmembrane protein. The suppression of p185 expression may be readily assessed by a number of available methods, including most conveniently, electrophoretic gel analysis to determine a reduction in p185 levels. It is proposed that the same means of introducing the E1A gene, or its products, will be applicable in these further embodiments as discussed in connection with the transformation embodiments above.

FIG. 1(A–B). (a) Transcriptional repression of neu promoter by E1A gene products. Rat-1 cells were transfected with 5 μg of the pNeu-EcoR1-CAT construct, which contains the CAT gene driven by neu oncogene promoter containing 2.2-kb upstream DNA sequences. Lane 1, basal neu promoter activity (its relative CAT activity is defined as 100%); lanes 2–4, CAT activity after cotransfection with 10 μg of carrier DNA pSP64 vector (102%, lane 2); E1A-expressing plasmid pE1A (34%, lane 3); pE1Apr, a plasmid containing only the E1A promoter (98%, lane 4). The CAT activities of a reporter plasmid, RSV-CAT, containing the CAT gene under the control of RSV LTR (10%, lane 5) were not significantly changed by cotransfection of 10 μg of pE1A (98%, lane 6) or 20 μg of pE1A (96%, lane 7).

(b) Effect of various adenovirus early genes on neu promoter activity. The pNeuEcoRI-CAT was cotransfected with pSP64 vector or plasmid expressing various adenovirus early genes, E1A, E1b, E2A, and E3, as indicated. The relative CAT activities are as follows: SP64, 100%; E1A, 35%, E1B, 97%, E2A, 99%, E3, 102%. RSV-CAT was used as a positive control.

FIG. 2(A–E). Transient expression from neu promoter with cotransfection with increasing amounts of pE1A (a), pE1A-13S (b), pE1A-12S (c), and pE1Ad1346 (d). A constant amount (5 μg) of the pNeuEcoR1-CAT construct was cotransfected into Rat-1 cells with 5, 10, 15, and 20 μg of the test constructs. The total amount of the transfected DNA were kept constant by adding the appropriate amount of carrier DNA pSP64. The relative CAT activities without E1A (lanes 0 in a–d) are defined as 100%. The relative CAT activities with 5, 10, 15 and 20 μg of test constructs are as follows: E1A, 68%, 35%, 26%, 17%; E1A-13S, 72%, 48%, 36%, 24%; E1A-12S, 66%, 46%, 28%, 21%; E1Ad1346, 102%, 103%, 99%, 102%, (e) Summary of the effects of different E1A mutants on transient expression from the neu promoter. Schematic structures of the proteins encoded by different E1A mutants are shown on the bar diagram. Hatched areas represent the conserved protein regions of the E1A products. Bar diagrams are not drawn to scale.

FIG. 3(A–B). Localization of E1A-responsive DNA element in the upstream region of neu promoter.

(a) Schematic maps of the neu promoter 5′ deletion constructs that were fused individually to the CAT gene to create the plasmids as indicated by the names of the restriction enzymes used for generating the constructs.

(b) Level of expression of the CAT gene directed by each of the promoter fragment constructs after transfection of 5 μg of the plasmids into Rat-1 cells with 10 μg of cotransfected pE1A (E) or carrier DNA pSP64 (c). The names of restriction enzymes above each triplet assay refer to the constructs indicated in the maps.

FIG. 4(A–B). Derepression of neu by cotransfection of competing amounts of Stu I-Xho I neu promoter fragments.

(a) Rat-1 cells were transfected with 5 μg of the pNeuEcoR1-CAT plasmids giving basal neu promoter activity (lane 1); the repressed CAT activity after cotransfection with 5 μg of the pE1A is shown in lane 2. Plasmids pSP64/Stu-Xho containing the Stu I-Xho I neu promoter fragment cloned in pSP64 were cotransfected with pNeuEcoR1-CAT and pE1A. Lanes 3–6 show the competitive effects of increasing amounts (5, 10, 15, and 20 μg, respectively) of pSP64/Stu-Xho. Plasmids pSP64/R1-Xba containing the EcoRI-Xbu I neu promoter fragment were also cotransfected with pNeuEcoR1-CAT and pE1A. Lanes 7–9 show CAT activities from neu promoter by cotransfecting 5, 10, and 20 μg of pSP64/RI-Xba, respectively. The relative CAT activities of lanes 1–9 are as follows: 100%, 32%, 27%, 31% 58%, 79%, 38%, 31%, 24%.

(b) Immunoblot for p185 protein in the cell lysates of SK-BR-3 breast cancer cells transfected by pNeuEcoRV-CAT. Seventy-five micrograms of protein from each sample was electrophoresed on 7% SDS/PAGE gels prior to transfer on nitrocellulose. Filters were blotted with the primary antibody mAb-3. Lane 1, lysates of SK-BR-3 cells transfected with 5 μg of pE1A; lane 2, cotransfected with 5 μg E1A and 20 μg of pSP64/RI-XbaI; lane 3, cotransfected with 5 μg of E1A and 20 μg of pSP64/Stu-Xho; lane 4, lysates of SK-BR-3 cells after mock transfection. The protein size marker is shown on the right. The arrow indicates the position of p185 protein. The p185 protein bands were scanned by Bio-Rad video densitometer model 620 to determined the relative p185 protein level. The p185 protein level in the mock transfection sample is defined as 100% and the relative amounts of p185 proteins in lanes 1–3 are 57%, 54%, and 89%, respectively.

Figure 5:
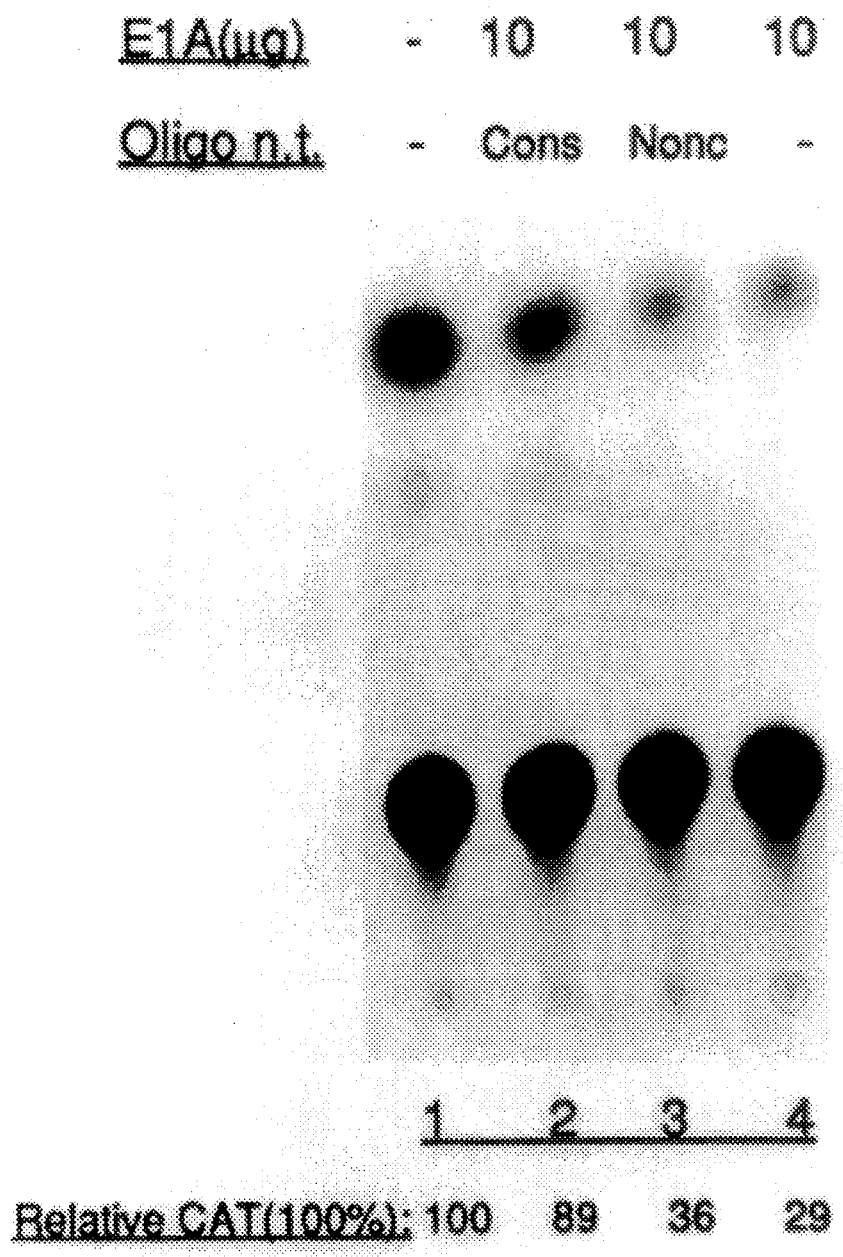

FIG. 5. Removal of the E1A-mediated repression of neu by cotransfection of a 20-mer oligonucleotide containing the consensus sequence. Rat-1 cells were transfected with 3 μg of pNeuEcoRV-CAT plasmids, giving basal neu promoter activity (lane 1); CAT activity after cotransfection with 10 μg of pE1A is shown in lane 4. Two micrograms of the 20-mer double-stranded oligonucleotide containing the consensus sequence (lane 2, Cons) was cotransfected with pNeuEcoRV-CAT and pE1A (molar ratio of oligomer:pNeuEcoRV-CAT=35:1), resulting in significant derepression; cotransfection of 2 μg of a 22-mer random nonhomologous oligonucleotide with pNeuEcoRV-CAT and pE1A had no significant derepression effect (lane 3, None). The values for relative CAT activity are the average of three experiments. The upper strand sequence of the synthetic 20-mer oligonucleotide is shown at the bottom; the proposed E1A-responding sequence is underlined.

FIG. 6(A–D). (a) Southern blot analysis of NIH3T3, B104-1-1 and their transfectants using an EcoRI-SstI E1A DNA probe. 10 μg of genomic DNA from the indicated cell lines were digested to completion with EcoRI+SstI restriction endonucleases and subjected to electrophoresis on a 1% agarose gel. The DNAs were transferred to Nitran filter paper and hybridized with the E1A probe. The DNA markers are shown on the left.

(b) Immunoblot analysis for E1A proteins in the cell lysates of the indicated cell lines. 50 μg of each sample were electrophoresed on 10% SDS-PAGE prior to transfer to nitrocellulose. Filters were incubated with the primary antibody M73 against E1A, obtained from Dr. L. S. Chang of Ohio State University. The protein molecular weight marker and the position of E1A proteins are shown on the right. 25 μg of Cell lysate from 293 cells was used as a positive control.

(c) Immunoblot analysis for the neu encoded p185 protein in the cell lysates of the indicated cell lines. The experiments were performed as described in section (b) above. The primary antibody was mAB-3 against p185, purchased from Oncogene Science Inc.

(d) Southern blot analysis of the indicated cell lines using rat neu DNA probe. The experiments were performed as described in section (a) above. The DNAs were digested with Bam HI restriction endonuclease.

FIG. 7(A–F). Morphologic effects of E1A expression in neu-transformed B104-1-1 cells: (a) B104-1-1; (b) B-E1Apr; (c) N-E1A-1; (d) B-E1A-1; (e) B-E1A-2; (f) B-E1A-3 (Magnification: X130).

FIG. 8(A–B). (a) [$^3$H] Thymidine Incorporation of the indicated cell lines. 9×10$^3$ cells were plated in 96 well multiwell plates and cultured in Dulbecco's modified Eagle medium supplemented with 10% calf serum for 16, 40 and 64 hrs. Cell received a 2 hr pulse of 1 μCi [$^3$H]-thymidine per well to label those that were synthesizing DNA prior to harvest. Radioactivities of individual samples were counted by scintillation counter. Average cpm counts were calculated from replicated samples.

(b) Anchorage independent growth of E1A-transfected B104-1-1 and NIH3T3 cells. 1×10$^3$ cells were plated in 0.35% soft agar over a 0.7% agar lower layer. Colonies were counted after 4 weeks. A typical plate and the mean of triplicate samples plus or minus the standard error of the mean are shown for each group.

Figure 9B:
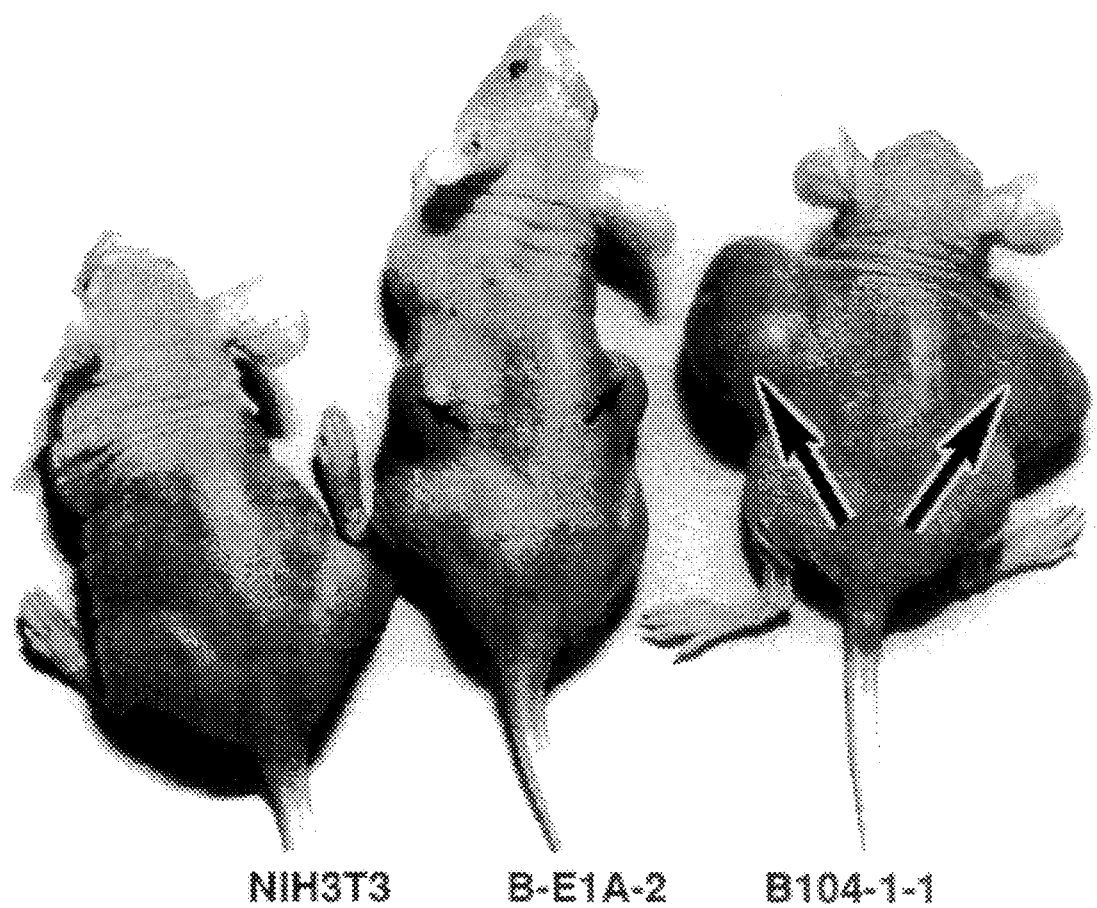

FIG. 9(A–B). (a) Summary of tumorigenicity of B104-1-1, NIH3T3 and their transfectant. 1×10$^5$ viable cells were injected subcutaneously into right and left flanks of female homozygous nu/nu mice, respectively. Tumor formation was scored at indicated days as presence or absence of a visible tumor mass. 16 days after injection, tumor volumes were estimated as the product of tri-dimentional califer measurements (longest surface length and width, and tumor thickness). N.D.: not detectable at the time of evaluation.

(b) A representative result of tumorigenicity study. From right to left: the animals were injected with B104-1-1, B-E1A-2 or NIH3T3 cells 18 days prior to the photographing data.

FIG. 10(A–C). (a) E1A gene products inhibited the cell motility of the neu-transformed 3T3 cells. N-E1A: NIH3T3 cells transfected with E1A; B-neo: B104-1-1 cells transfected with neomycin resistant gene; B-E1A-1 to 5: five independent cell lines generated by transfecting E1A gene into B104-1-1 cells. The motility assays were carried out by using transwell unit with 5 µm pore size polycarbonate filter in 24 well cluster plate (Costar). Lower compartment of the transwell contained 600 µl of one of the chemoattractants: 20 µm fibronectin (FN) or 100 µm FN dissolved in DMEM/F12, or hepatic endothelial cell conditioned media (HSE), or DMEM/F12 medial only as negative control. The cells. ($3\times10^4/0.1$ ml in DMEM/F12) were plated in the upper compartment and incubated for 6 hrs at 37° C. in a humidified 5% $CO_2$ atmosphere. After the incubation, the filters were fixed with 3% glutaraldelyde in PBS buffer and stained with Geimsa. ach sample was assayed in triplicate and cell mitility was measured by counting the number of cells that had migrated to the lower side of the filter. At least four HPFs were counted per filter. The number of cells migrated to DMEM/F12 has been deducted from each sample to eliminate the background and all the assays were done in triplicates.

(b) E1A gene products inhibited the invasiveness of the neu-transformed 3T3 cells. The assay of in vitro invasiveness was done basically as described by Albini et al. 1987 and Repesh. 1989. The basement membrane preparation, matrigel, was purchased from Collaborative Research, Inc. Filters in the transwell unit (same as used in motility assay) were coated with 0.1 ml of 1:20 dilution of matrigel in DMDM/F12 media. Lower compartment contained 0.6 ml of HSE as chemoattractant or DMEM/F12 as negative control. The cells ($5\times10^4/0.1$ ml in DMEM/F12) were plated in upper compartment and incubated for 72 hrs at 37° C. in a humidified 5% $CO_2$ atmosphere. Cells were fixed, stained and counted as described in 1.a. All the assays were done in triplicate and assays were repeated twice.

(c) Gross appearance of lungs from the mice injected with B-neo cells (1), N-E1A cells (2), B-E1A-1 cells (3), and B-E1A-2 cells (4); E1A gene products inhibited the lung colonization of neu-transformed cells. See legend for table 1 for experimental details.

Figure 11A:

FIG. 11(A–B). E1A suppresses neu-induced tumour formation and metastasis in vivo in nude mice.

(a) Top, animal injected with B104-1-1 cells, a neu oncogene transformed NIH3T3 cell line; Bottom, animal injected with B-E1A2 cells, an E1A transfectant of B104-1-1. Photographs were taken 18 days after injection, and results are representative of other tumourigenicity studies.

(b) Left, gross appearance of lungs from mice injected with B104-1-1 cells; Right, gross appearance of lungs from mice injected with the E1A transfected cells, B-E1A2. Mice were inoculated with $1\times10^5$ cells/0.1 ml in PBS via the lateral tail vein at day 0, and were sacrificed 21 days after injection. The numbers of lung tumour nodules were determined following infiltration with India ink, only those lung nodules greater than 1 mm in diameter were counted in the assay.

The neu oncogene is a transforming gene originally identified from rat neuro/glioblastomas (Shih et al., 1981). Subsequently, both the activated neu oncogene and its normal cellular counterpart, the normal neu gene, were cloned from rat and human libraries (Bargmann et al. 1986; Coussens et al. 1985; Hung et al. 1986; Yamamoto et al., 1986). The neu gene encodes a 185-KDa transmembrane protein (p185) which is related to, but distinct from the epidermal growth factor receptor (EGF-r). The neu encoded p185 and EGF-r have identical gross structural organization including ligand-binding, transmembrane and intracellular kinase domains and also share extensive sequence homology, specifically, >80% of the amino acids in the tyrosine kinase domain are identical. Recently, the ligand for the neu-encoded p185 protein has been functionally identified in rat cells and isolated from human breast cancer cells, which will facilitate the better understanding of the function of the neu- encoded p185 protein in normal and malignant cell growth and development (Lupu et al, 1990; Yarden et al. 1989).

The activated neu oncogene contains a single amino acid substitution in the transmembrane domain and possesses an increased tyrosine kinase activity when compared to its normal counterpart. Furthermore, it has demonstrated that amplification of the neu protooncogene facilitates oncogenic activation by a single point mutation (Hung et al., 1989). the human homologue of the rat neu oncogene, also named as HER-2 or c-erbB2, has been shown to be amplified/overexpressed in 25–30% of human primary breast cancers and ovarian cancers (Hung et al., 1988; Slamon et al., 1987). Breast cancer patients with neu overexpression show a significantly lower overall survival rate and a shorter time to relapse than those patients without neu overexpresson, suggesting that neu overexpression may be used as a prognostic factor (Id.). Amplification/overexpression of the human neu gene has also been shown to correlate with the number of axillary lymph nodes positive for metastasis in breast cancer patients (Id.). These studies strongly suggest that the neu oncogene may play an important role in malignant transformation and metastasis.

The primary function of the adenovirus E1A gene is to activate other adenoviral genes during a permissive viral infection by modifying the host cell transcriptional apparatus, thereby resulting in host cell immortalization of transformation by the whole adenoviral early region (Berk et al., 1986). Although both transcriptional activation and transcriptional repression of non-adenoviral genes by the E1A proteins have been reported (Borrelli et al., 1984; Hen et al., 1985; Lillie et al., 1989; Sassome-Lorsi et al., 1987; Stein et al., 1987), their functional significance and physiological impact is unclear in many cases. Interestingly, it has been shown that exogenously added E1A gene can reduce the metastatic potential of ras transformed rat embryo fibroblasts (REF) cells by activating the cellular nm23 gene which is a lately cloned and characterized cellular metastatic suppressor gene (Pozzaati et al., 1988). Additionally, the transfected E1A gene has been shown to repress secreted protease gene expression at the transcriptional level and inhibits metastasis of human tumor cells (Liotta, 1989).

Recently, the present inventors have studied the effects of the E1A gene products on the promoter activity of the neu gene and found that E1A proteins can repress the expression of both human and rat neu oncogene at the transcriptional level. Since both the neu gene and the E1A gene are well-known transforming oncogenes, these findings raised an interesting question: Is it possible that the E1A proteins may act as transformation suppressor for the neu-transformed cells via transcriptional repression?

To address this question, the inventors undertook to develop a biological functional assay system in which the effects of E1A could be studied. The E1A gene was introduced into the neu transformed B104-1-1 cells to generate a derivative that stably express the E1A gene products, these cells were termed B-E1A cells. The transformed phenotypes of the parental neu-transformed B104-1-1 cell line and the B-E1A cell lines could then be compared following injection of each cell type into nude mice. The findings dramatically demonstrated that the E1A gene products can act as suppressors of neu oncogene-mediated cell transformation and metastasis.

The Examples which follow set forth studies wherein the inventors demonstrate the ability of the E1A gene to suppress neu gene expression (Example I), neu gene-mediated tumorigenicity (Example II), and neu gene-mediated metastasis (Example III). While these studies are believed to be exemplary of the invention, it will be appreciated by those of skill in the art that many modifications and alterations may be made in these embodiments without departing from the spirit and scope of the invention.

EXAMPLE I

Transcriptional Repression of the neu Protooncogene by Adenovirus 5 E1A Gene Products This Example relates to studies conducted by the inventors which demonstrate that the adenovirus E1A 12S and 13S products are effective in repressing the transcriptional activity of the neu promoter. In particular, it is demonstrated that the conserved region 2 (CR2) of the E1A proteins are required for repression. Moreover, these studies indicated that a cis-acting DNA element in the upstream region of the neu promoter is responsible for the trans inhibition of the promoter by the E1A gene products.

1. Materials and Methods
  a. Plasmids

The recombinants used in this study have been described. pE1A (Chang et al., 1989; Hearing et al., 1985) is a plasmid expressing only the E1A region gene; pE1A12S and pE1A13S (Hearing et al., 1985) express 12S E1A protein and 13S E1A protein, respectively; pE1A-d1343 (Hearing et al., 1985) contains a 2-base-pair (bp) frameshift deletion in the E1A coding sequences (adenovirus nucleotide sequence positions 621 and 622); pE1A-d1346 (Hearing et al., 1985) contains an in-frame deletion of nucleotides 859–907 (48 bp), resulting in the deletion of 16 amino acids inside the CR2 of the E1A proteins; pE1Apr contains only the E1A promoter (−499 to +113 relative to the E1A cap site); pE2A-CAT (Chung et al., 1989) is a reporter plasmid containing E2 early promoter fused with the chloramphenicol acetyltransferase (CAT) reporter gene; pRSV-CAT is a reporter plasmid containing the CAT gene under the control of the Rous sarcoma virus (RSV) long terminal repeat (LTR); pE1B, pE2, and pE3 are plasmids expressing E1B, E2, and E3 genes, respectively. pNeuEcoR1-CAT contains the 2.2-kilobase (kb) rat neu promoter and upstream sequences linked to the CAT gene. The deletion mutant of the neu promoter used in this study are described in the legends to FIG. 3 and 4a. pRSV-β-gal contains the RSV LTR linked to β-galactosidase gene used as an internal control for transfection efficiency.

b. Cell Cultures

Cell cultures were performed as described (Hung et al., 1989; Matin, et al., 1984). The Rat-1 and SK-BR-3 cells were grown in dulbecco's modified Eagle's medium (DMEM) supplemented with 10% calf serum and fetal calf serum, respectively.

c. DNA Transfection

All transfections were carried out with the calcium phosphate precipitation technique of Graham and Van der EB as modified by Anderson et al. (Hung et al. 1989; Anderson et al., 1979; Ausubel et al., 1987). In each transfection, $8 \times 10^5$ Rat-1 cells or $2 \times 10^6$ SK-BR-3 cells (2×10 cm dishes) were seeded 24 hr before transfection. Total transfection DNA was kept constant (maximum, 30 μg) among different samples in the same experiment by adding approximate amounts of carrier DNA (pSP64).

d. CAT Assays

Cell extracts were prepared 40 hr after transfection. Portions of cell lysates were assayed for β-galactosidase activity from the cotransfected pRSV-β-gal plasmid. All CAT assays (Gorman et al., 1982) were normalized to the internal transfection efficiency control. The CAT assay monitors acetylation of [$^{14}$C]chloramphenicol in cell extracts; [$^{14}$C]-chloramphenicol and its products are separated by thin-layer chromatography (TLC) and visualized by autoradiography. Individual spots on TLC paper were cut, their radioactivities were assayed by liquid scintillation spectrometry, and the relative CAT activities were calculated accordingly. Each experiment has been reproducibly repeated at least three times and a representative of several experiments is shown.

e. Immunoblot

SK-BR-3 cell lysates were made 40 hr after transfection and immunoblots were performed as described (Matin et al., 1984). The mAB-3 monoclonal antibody against the human neu gene product—p185 protein—was purchased from Oncogene Science.

2. Results a. Transcriptional Repression of neu by the Adenovirus 5(AD5) E1A Products A DNA segment of 2.2 kb containing the neu promoter and upstream sequences was fused with the CAT expression vector to generate the pNeuEcoR1-CAT plasmid. In transient-expression assays using Rat-1 cells (FIG. 1A), a cotransfection of pNeuEcoR1-CAT with pE1A, a plasmid expressing the E1A gene, led to a significant decrease of CAT activity. Cotransfection with pSP64, a plasmid vector, had no effect on CAT activity. To rule out the possibility that decreased transcription from neu promoters could be due to the titration of cellular transcription factors by the cotransfected E1A promoter, a deletion mutant, pE1Apr, which contains only the E1A promoter, was cotransfected with pNeuEcoR1-CAT. No effect on CAT activity was observed. A reporter plasmid containing the CAT gene under the control of the RSV LTR was not E1A responsive, indicating that decreased CAT expression was not due to a general decrease of transcription by E1A.

Figure 1B:
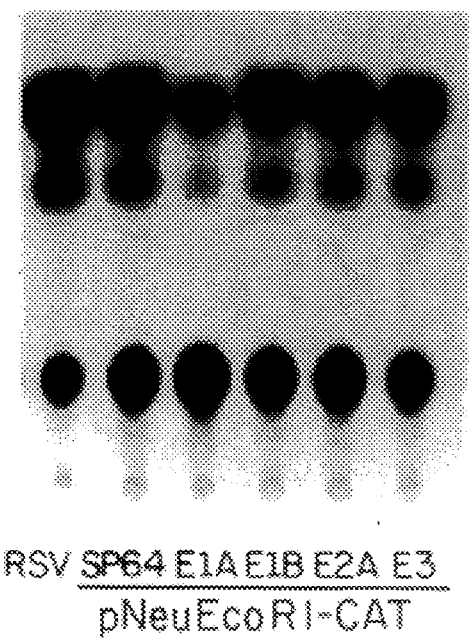

In parallel experiments, stimulation of transcription from the E2A transcription unit by the E1A products was assayed by cotransfecting pE1A and pE2A-CAT (CAT gene driven by E2 early promoter). The results showed that repression of neu and transactivation of E2A promoter occur in the same range of pE1A concentration. To see if other adenovirus early genes can repress the neu promoter, plasmids expressing the early genes of adenovirus individually were cotransfected with pNeuECoR1-CAT (FIG. 1b). No change in CAT activity was observed with E1B, E2, or E3 alone, indicating the among these early genes of adenovirus, only the E1A gene could function as a repressor of the neu promoter.

b. Repression of neu Is E1A Concentration Dependent and Requires the E1A Conserved Region 2.

Figure 2A:
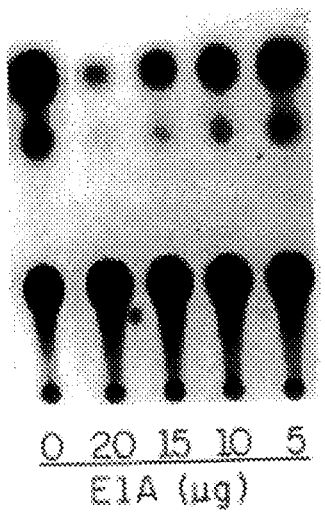

To further study the interactions of E1A genes products with the neu promoter, increasing amounts of pE1A were cotransfected with pNeuEcoR1-CAT in ratios of 1:1, 2:1, 3:1, and 4:1 (FIG. 2a). Inhibition of the gene expression directed by the neu promoter was found to be dependent on pE1A concentration, and 50% repression could be observed at as low as a 1:1 ratio of pE1A:pNeuEcoR1-CAT.

Figure 2B:
Figure 2C:
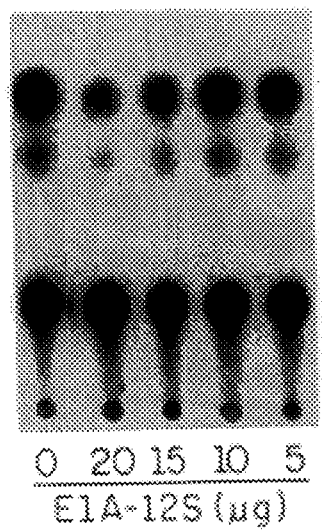

The Ad5 E1A gene produces two major spliced products, the 12S and 13S mRNAs, that encode proteins 243 and 289 amino acids long, respectively (Moran et al., 1987). To determine which E1A gene product was responsible for the observed repression, the same experiments were performed with recombinant plasmids expressing either 12S or 13S E1A gene product (pE1A-12S and pE1A-13S). As shown in FIG. 2b and c, both the 12S and 13S products were effective at repressing neu transcription in a concentration-dependent manner.

The E1A gene products contain three highly conserved regions; CR1, CR2, and CR3 (Moran et al., 1987;.Van Dam et al., 1989). CR1 and CR2 exist in the 12S and 13S, whereas CR3 is unique to the 13S product. Since 12S itself can repress neu efficiently, the inventors reasoned that the CR3 is dispensable for transcriptional repression of neu by E1A.

Figure 2D:
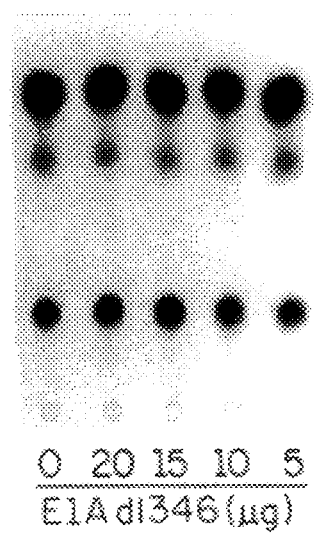
Figure 2E:
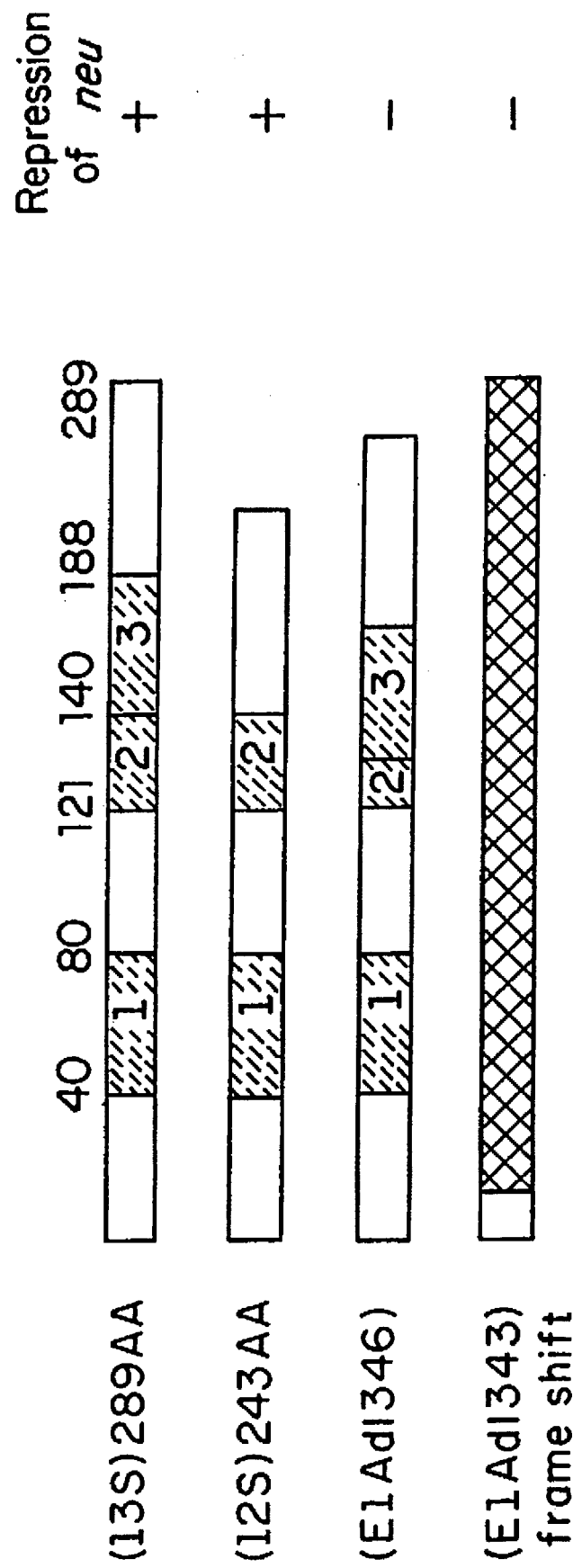
Figure 3A:
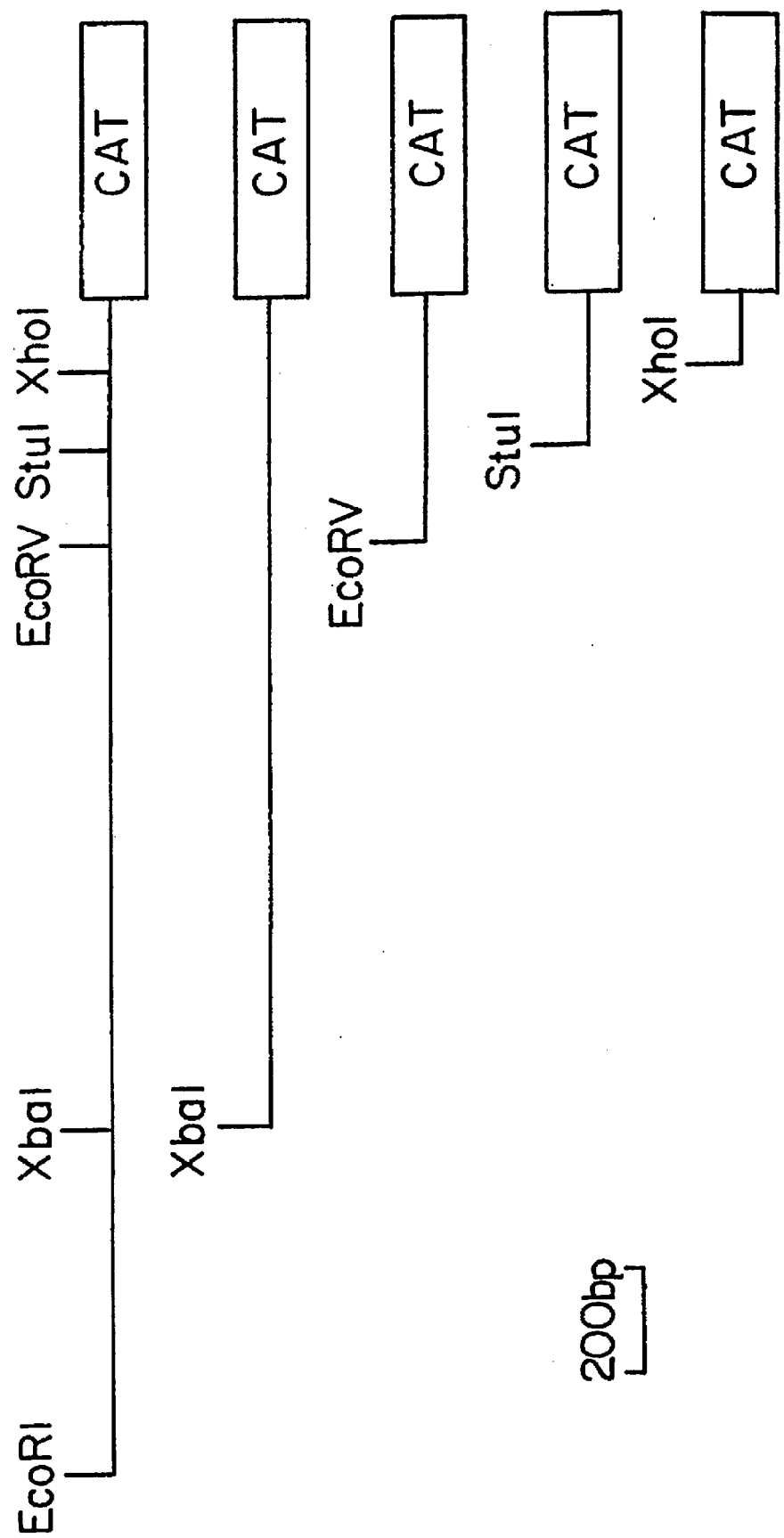
Figure 3B:
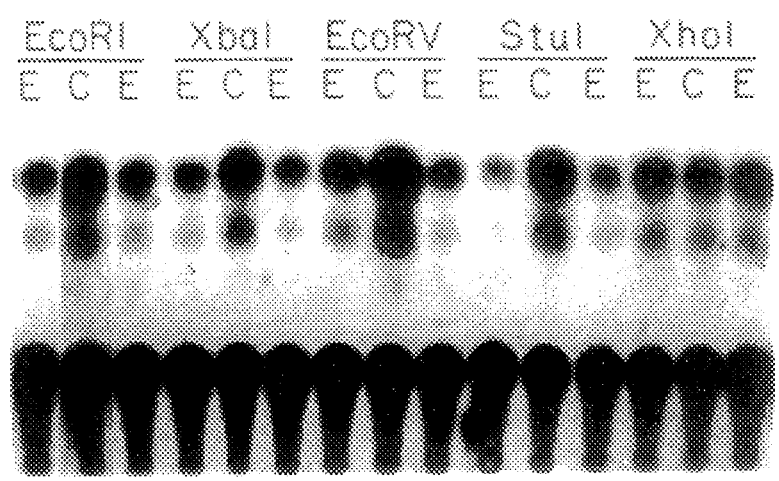

To further localize whether the CR1 or the CR2 in the E1A protein was required for efficient repression of neu, parallel experiments were performed using deletion mutants pE1Ad1343 and pE1Ad1346 (Hearing et al., 1985). The pE1Ad1343 mutant contains a 2-bp deletion in the E1A coding sequence, resulting in a frame shift in all three conserved regions of the E1A products and leaving only the N-terminal 40 amino acids intact. No effect on CAT activity was observed when pE1Ad1343 mutant was cotransfected with pNeuEcoR1-CAT. The pE1Ad1346 mutant containing an in-frame deletion, which removed 16 amino acids within the CR2 but reserved the CR1, failed to express neu transcription (FIG. 2d). The inventors concluded that the CR2 of E1A gene products is required for efficient transcriptional repression of neu (FIG. 2E).

c. Localization of Target DNA Element in the neu Promoter Responding to E1A Repression To localize the DNA element in the neu promoter that mediates the transcriptional repression by the E1A products, a series of 5' deletion constructs containing portions of the neu promoter linked to a functional CAT gene were cotransfected with pE1A into Rat-1 cells (FIG. 3a). The transient expression of the CAT gene driven by each of these promoter fragments after transfection with control plasmid vector pSP64 or with pE1A in a ratio of 1:2 is shown in FIG. 3b. Only the pNeuXhoI-CAT containing the smallest promoter fragment was not repressed by E1A. Clearly the activity of a site within the Stu I-Xho I restriction fragment is sensitive to E1A repression. This Stu I-Xho I fragment is sensitive to E1A repression. This Stu I-Xho I fragment is located between −198 and −59 with respect to the transcriptional start site of neu. The inventors concluded that the target DNA element responding to E1A repression resides inside this 139-bp Stu I-Xho I fragment.

d. Evidence for the Involvement of Trans-Acting Factor (s)

Figure 4A:
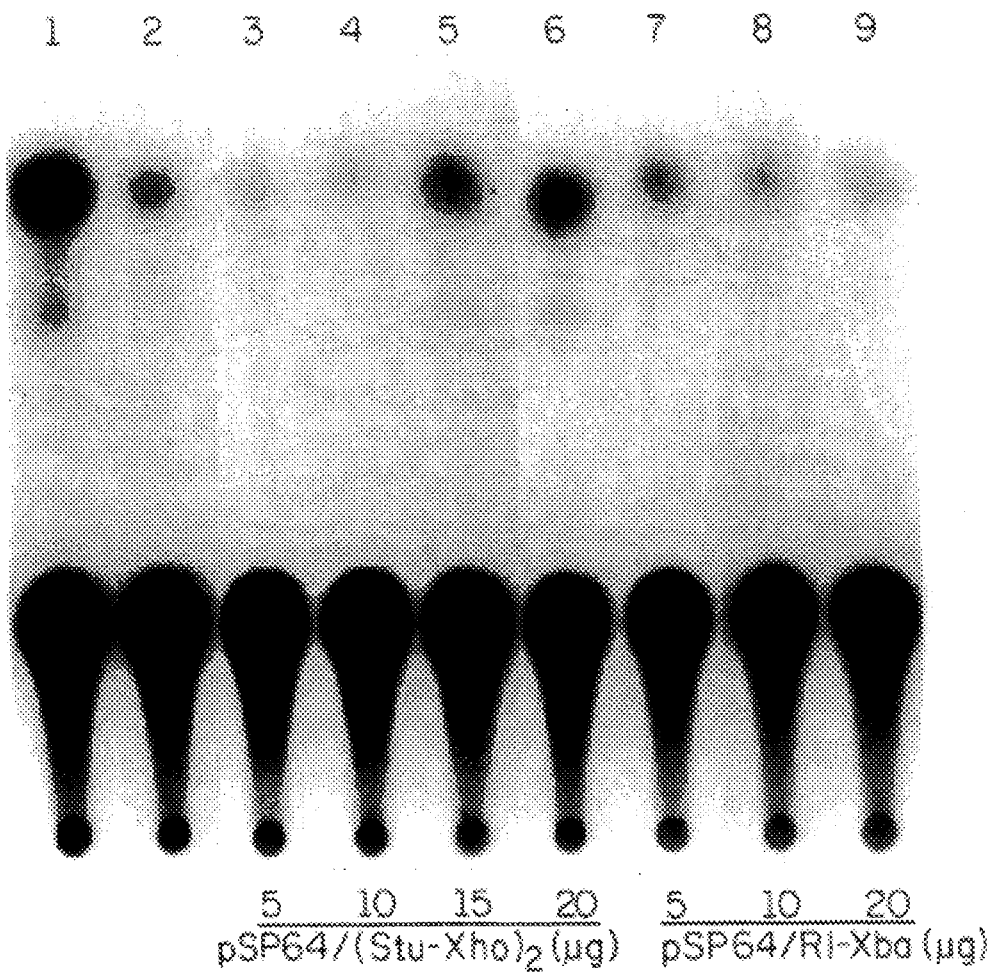

To examine whether this repression by the E1A products is a trans-acting process, the inventors attempted to remove the repression by cotransfecting a third recombinant, pSP64/Stu-Xho, containing only the Stu I-Xho I restriction fragment cloned in pSP64. Increasing amounts of pSP64/Stu-Xho, in cotransfections in which transcription of pNeuEcoR1-CAT was repressed by pE1A, relieved the repression of neu transcription in a concentration-dependent manner (FIG. 4a). In contrast, no derepression was observed when pSP64/RI-Xba containing the EcoRI-XBA I restriction fragment cloned in pSP64 was cotransfected. The derepression was effective at a 4:1 ratio of pSP64/Stu-Xho:pNeuEcoR1-CAT (FIG. 4a, lane 6), indicating that the Stu I-Xho I fragment can efficiently compete with the neu promoter for the transcription factor(s) involved in the repression of neu by E1A. These results confirm that the target for the E1A repression in the neu promoter is a cis DNA element within the Stu I-Xho I fragment of this promoter. Furthermore, this repression of transcription may involve an interaction between the DNA element and either the E1A products or some cellular transcription factors(s) interacting with or induced by the E1A products.

e. Repression of Human neu Expression in SK-BR-3 Cells

Comparison of the Stu I-Xho I fragment of rat neu promoter sequence with its counterpart sequence in human neu promoter (Tal et al., 1982) reveals >86% homology. It was suspected by the inventors that the human neu gene might also be repressed by E1A at transcriptional level by way of similar mechanisms. If this is the case, cotransfection of the Stu I-Xho I fragment of rat neu promoter might be able to relieve the repression of human neu incurred by E1A.

Figure 4B:
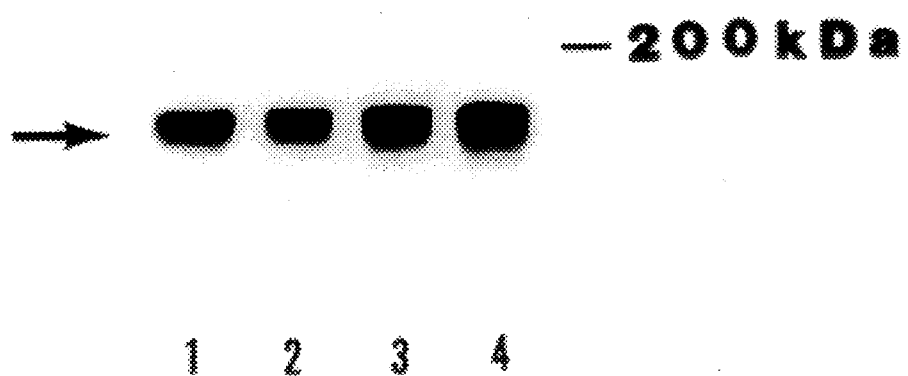

To test this possibility, cotransfection experiments were carried out by using as recipient cells human breast cancer cell line Sk-Br-3, which is known to overexpress human neu mRNA and p185 proteins (Kraus et al., 1987). Immunoblotting experiments with SK-BR-3 cell lysates showed that the expression of human neu gene products, the p185 protein, was reduced by introduction of E1A (FIG. 4b, compare lane 1 with lane 4). Cotransfection of pSP64/R1-Xba plasmids with pE1A at a 4:1 ratio was ineffective in removing the repression of p185 expression by E1A, whereas cotransfection of pSP64/Stu-Xho with pE1A at the same ratio relieved the repression by E1A.

It is known that the maximum efficiency of transient transfection can reach only 50% (Chen et al., 1988); the other 50% of nontransfected Sk-Br-3 cells should still produce high levels of p185 proteins, which can result in high background in the E1A-mediated repression of p185. Therefore, the repression effect on the endogenous neu-encoded p185 by transiently transfected E1A in the immunoblotting assay was not as dramatic as that observed in CAT assays. However, the small difference was detected reproducibly. The best interpretation of the results is that E1A can repress human neu promoter at transcriptional level by targeting at the cis-acting DNA element in human neu promoter corresponding to the Stu I-Xho I fragment of rat neu promoter.

f. The Sequence TGGAATG is an Important Site for the E1A-Mediated Repression

E1A has been reported to repress enhancer mediated transcription activation of simian virus 40 (Borrell et al., 1984), polyomavirus (Velcich et al., 1986), immunoglobulin heavy chain (Hen et al., 1985), and insulin genes (Stein et al., 1987). Comparison of the enhancer sequences of these genes reveals a consensus sequence (shown overleaf), which is likely to be the core sequence of the E1A-responding element.

AAA
(G)TGGTTT(G)

However, there has been no experimental evidence to support this notion. A sequence, TGGAATG, that matches the consensus sequence has been fund in the Stu 1-Xho 1 E1A-responding element of the rat neu promoter. An identical sequence also exists in the corresponding region of the human neu promoter (Tal et al., 1987). It is therefore conceivable that the sequence TGGAATG may be an important target sequence for the E1A-induced repression.

To investigate this possibility, a 20-mer oligonucleotide from the rat neu promoter containing the sequence TGGAATG was synthesized (FIG. 5). This oligonucleotide efficiently competed with the neu promoter for the transcriptional factors(s) involved in the repression of neu by E1A, resulting in a derepression effect (FIG. 5, lane 2), whereas a 22-mer random nonhomologous oligonucleotide had no derepression effect (FIG. 5, lane 3). These data provide experimental evidence that the 20-mer oligonucleotide harbors a critical sequence required for the E1A-induced inhibition. Since the sequence TGGAATG within this 20-mer oligonucleotide resembles the consensus sequence in the enhancer sequences of other genes that can be repressed by E1A, it is likely that this 7-bp sequence is the critical sequence that is mediating the E1A effect.

3. Discussion

The foregoing results show that in a cotransfection system, the E1A gene products repressed the neu expression at the transcriptional level. It is further demonstrated that the repressive effect on neu expression is lost in E1A products when part of the CR2 (amino acids 120–136) is deleted. Notably, a structure motif in this deleted part of the adenoviral E1A CR2 region is shared among the papovaviral large tumor antigens, the v- and c-myc oncoproteins, the E7 transforming proteins of human papilloma viruses, and the yeast mitotic regulator DCD25 gene product (Figge et al., 1988). This region encoding the shared motif is also required by E1A, simian virus 40 large tumor antigen, and human papilloma viruses 16 E7 for their specific binding to the human retinoblastoma gene product, RB protein (Whyte et al., 1988; Whyte et al., 1989).

These studies further elucidate the oligonucleotide sequence mediating E1A-induced repression in the upstream region of neu promoter. The sequence TGGAATG is perfectly conserved between rat and human neu promoter, which is indicative of functional importance. In addition, this sequence matches the consensus sequence of other genes that can also be repressed by E1A at transcriptional level. Taken together, these findings suggest that there may be common mechanisms involved in this type of E1A-mediated repression. It has been proposed that E1A may form a complex with cellular transcription factor(s) and thereby modulate the specific binding of the transcription factor(s) to enhancer elements that are important for transcription (Mitchell et al., 1989). Identification of the defined DNA sequences responsible for the E1A-mediated inhibition of neu transcription will allow us to identify the transcription factor(s) involved in this process.

The neu protooncogene is notably amplified in patients with metastatic breast cancer. Expression of the E1A gene can inhibit experimental metastasis of ras oncogene-transformed rat embryo cells. Here, it is shown that neu transcription can be repressed by E1A products in an established rat embryo fibroblast cell line, Rat-1. Furthermore, the inventors have found that in SK-BR-3 human breast cancer cells expression of the p185 protein, the human neu gene product, was reduced by introduction of E1A gene. The derepression effect observed in the cotransfection experiment with the Stu 1-Xho 1 fragment has demonstrated that this reduction of p185 proteins is likely due to the similar transcriptional repression mechanisms.

EXAMPLE II

Adenovirus-5 E1A Gene Products Act as a Transformation Suppressor of Neu Oncogene In Example I, transcription of the neu protooncogene was shown to be strongly repressed by adenovirus-5 E1A gene products through the use of a transient transfection assay. In the present Example, the E1A gene has been stably introduced into the neu-transformed B104-1-1 cells, to demonstrate that E1A-mediated neu repression can suppress neu-mediated transforming activity. In these studies, cells that expressed E1A products possessed reduced transforming and tumorigenic activity, as evidenced using standard assays for each. These results demonstrated that E1A gene products can act negatively to suppress the transforming phenotype of the neu oncogene, and is believed to be the first example of a gene, i.e., the E1A gene, that can act in one setting as a transforming oncogene, and in another as a transforming suppressor gene.

The B104-1-1 cell line, an NIH3T3 transfectant that has approximately 10–20 copies of mutation-activated genomic neu oncogene has been shown to be highly transforming and tumorigenic (Bargmann et al., 1986; Stern et al., 1986). For the present studies, B104-1-1 cells and control NIH3T3 cells were transfected with either E1A plasmids expressing adenovirus-5 E1A gene, (pE1A), or a derivative plasmid containing only the E1A promoter without the E1A coding sequence (pE1Apr). Cells were cotransfected with pSV2neo plasmids carrying a neomycin resistant marker gene (Southern et al., 1982).

The transfections were carried out with the modified calcium phosphate precipitation procedure of Chen and Okayama (1988). In each transfection, $5 \times 10^5$ B104-1-1 cells or NIH3T3 cells ($2 \times 10$ cm dishes) were seeded 24 h before transfection. The cells were transfected with either 10 µg of the E1A expressing pE1A plasmid DNA or its derivative pE1Apr plasmid DNA, along with 1 µg of pSV2-neo plasmid DNA (Southern et al., 1982). Approximately 14 h post-transfection, cells were washed and cultured in fresh medium for 24 h and split at a 1:10 ratio. The cells were then grown in selection medium containing 500 µg/ml of G418 for 2–3 weeks and individual G418 resistant colonies were cloned using cloning rings and expanded to mass culture.

Three kinds of stable transfectants were thus established: (1) B-E1A transfectants: B104-1-1 transfectants harboring the E1A gene; (2) B-E1Apr transfectants: B104-1-1 transfectants containing E1A promoter sequence, which is used as a control cell line in this study; and (3) N-E1A transfectants: NIH3T3 cells transfected with the E1A gene.

Cells cultures were performed as described previously (Hung et al., 1989; Matin et al., 1989). The B104-1-1 cell line and NIH3T3 cell line were grown in Dulbecco's modified Eagle's medium (DMEM) supplemented with 10% calf serum in a humidified atmosphere at 5% $CO^2$ at 37° C. The B-E1A transfectants and N-E1A transfectants were grown under the same condition with addition of G418 (500 µg/ml) into the culture media.

FIG. 6 shows the molecular characterization of the representative stable transfectants used in this study, employing both Southern blot and immunoblot analyses. Southern blot analyses were performed essentially by published techniques as previously described (Zhang et al., 1989). Genomic DNAs extracted from cultured cells were digested overnight at 37° C. with a 2-fold excess of a restriction endonuclease (either EcoR1, Sst1, or BamH1). Ten µg of each sample were then resolved by electrophoresis on a 1% agarose gel and transferred to Nytran membrane (Schleicher & Schuell, Keen, N.H.) using a 10×SSC (1.5 m NaCl, 0.15M sodium citrate). The blotted DNA were hybridized under high stringent conditions (68° C.) with [$^{32}$P] radioactive probe ($1-5 \times 10^8$ CPM µg$^{-1}$) labeled by using Random Primed DNA Labeling Kit (Boehringer Mannheim Biochemicals, Indianapolis, Ind.). The blots were washed twice for 15 min each in 2×SSC, 0.1% SDS at room temperature, and then twice for 30 min each in 0.1×SSC, 0.1% SDS at 68° C. with constant agitation. The filters were dried at room temperature and then exposed to Kodak X-OMAT™ AR film at −80° C. for 1 to 3 days.

Immunoblot analysis were performed basically by published techniques (Towbin et al., 1979) as previously described (Matin et al., 1990). Confluent cells growing in 10 cm plates were lysed with RIPA-B buffer (20 mM sodium phosphate, pH 7.4, 150 mM NaCl, 5 mM EDTA, 1% Triton, 10 µg/ml Aprotinin, 2 mM PMSF, 10 µg/ml Leupeptin and 4 mM iodoacetic acid) and then centrifuged at 10×g for 20 min at 4° C. The protein concentration of the supernatants was determined by Bio-Rad protein assay (Bio-Rad Laboratories, Richmond, Calif.). 50 µg of each sample were subjected to SDS polyacrylamide gel electrophoresis (10%) and transferred to nitrocellulose. The nitrocellulose filters were treated with 3% nonfat dry milk in TPBS buffer (0.05% Tween-20, 138 mM NaCl, 2.7 mM KCl, 4.3 mM Na2HPO4.7H$_2$O and 1.4 mM KH$_2$PO4) for 1 h at room temperature, followed by an overnight incubation at 4° C. with primary monoclonal antibodies M73 against the E1A proteins (a gift of Dr. L. S. Chang., Ohio State Univ.) or mAb-3 against the neu encoded p185 protein (purchased from Oncogene Science Inc., Manhasset, N.Y.). After three 10 min washes with TPBS buffer, the nitrocellulose was then incubated for 1 h at room temperature with 1:1000 dilution of horseradish peroxidase-conjugated goat anti-mouse immunoglobulin (Bio-Rad Laboratories). The nitrocellulose filters were washed 3 times in TPBS buffer and were subjected to color developing reaction with horseradish peroxidase substrate (Kirkegaard & Perry Laboratories, Inc., Gaithersburg, Md.).

Figure 6A:
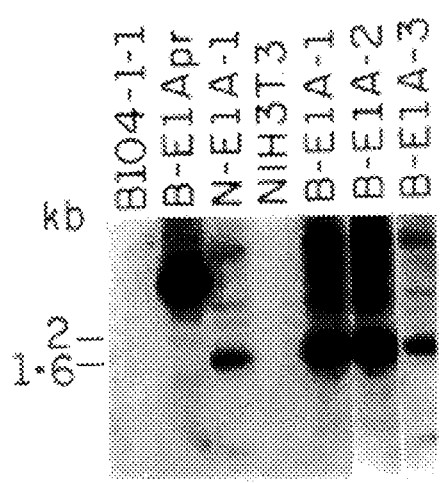
Figure 6B:
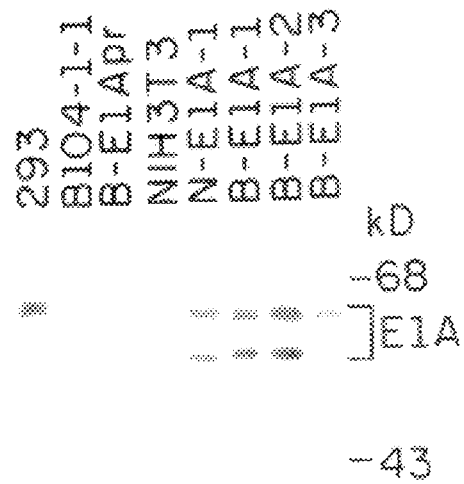

To assure that the exogenous E1A gene or E1A promoter DNA had integrated into the genome of the transfectants, DNA blot analysis with the E1A probe was performed and the results confirmed the integration of transfected foreign DNA (FIG. 6a). Noticeably, the three B-E1A transfectants studied (B-E1A-1, B-E1A-2 and B-E1A-3) acquired different copy numbers of the E1A gene. Immunoblot detection of E1A further confirmed that the B-E1A and N-E1A transfectants actually produced E1A proteins and the E1A protein levels in these transfectants are lower than that in the 293 cell line, an established cell line of primary human embryonal kidney transformed by adenovirus DNA. (FIG. 6b).

Figure 6C:
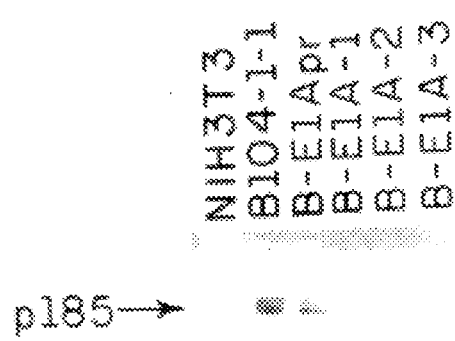
Figure 6D:
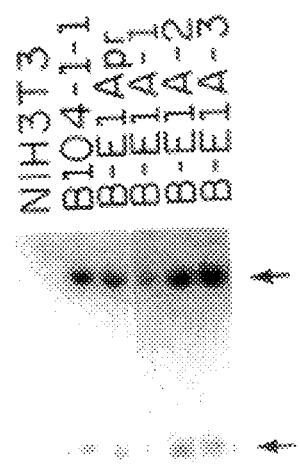
Figure 7A:
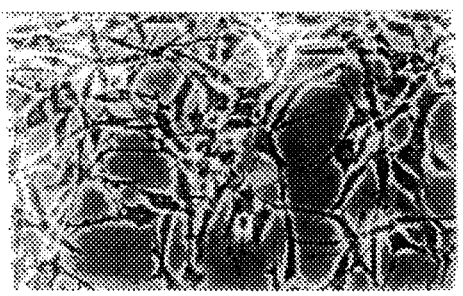
Figure 7B:
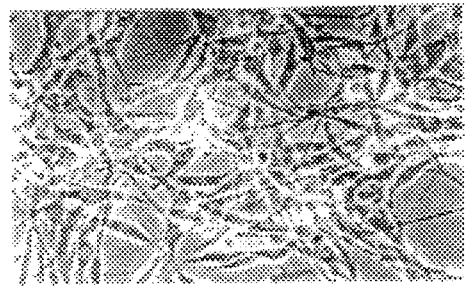
Figure 7C:
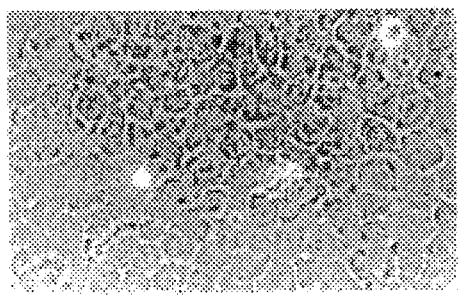
Figure 7D:
Figure 7E:
Figure 7F:
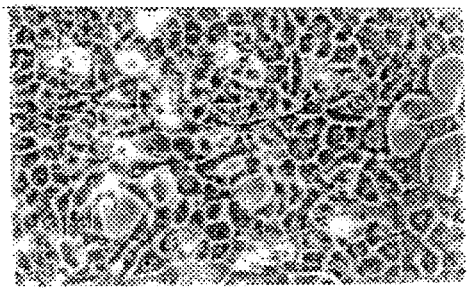

To examine if expression of E1A can inhibit neu expression, immunoblot analysis for the neu-encoded p185 protein was also performed and the p185 proteins were virtually undetectable in all the transfectants using horse radish peroxidase detection method (FIG. 6c). However, slightly higher levels of p185 proteins could be detected in B-E1A-3 than those in B-E1A-1 and B-E1A-2 when the more sensitive $^{125}$I-protein-A detection method was used. Since p185 proteins were barely detectable in B-E1A transfectants, DNA blot analysis for rat neu gene was conducted to make sure that the neu gene was not lost. As shown in FIG. 6d, the incorporation of E1A gene into the genome did not alter the neu gene at the DNA level.

Among the three B-E1A transfectants, B-E1A-2 and B-E1A-3 had levels of the neu gene that were comparable to those of the parental B104-1-1 cell line; while B-E1A-1 appeared to have a lower level neu gene. This may be due to partial loss of the neu gene in this line during the establishment of this transfected cell line. The three B-E1A transfectants shown in FIG. 6 were chosen for further transformation assay because they represented three different subtypes of B-E1A transfectants: (1) B-E1A-1 had fewer copies of neu gene compared to B104-1-1 and more copies of E1A gene; (2) B-E1A-2 retained the same level of neu as B104-1-1 and high levels of E1A gene; (3) B-E1A-3 contained the same amount of neu as B104-1-1, but a low quantity of the E1A gene.

The transforming phenotype of the neu-transformed cells usually includes a transformed morphology, non-contact-inhibited growth pattern, increased DNA synthesis rate, anchorage-independent growth and the ability to induce tumors in nu/nu mice. To determine the effect of E1A expression on the transforming ability of neu-transformed B104-1-1 cells, the B-E1A transfectants as well as the control cell lines were assayed for all the above mentioned transforming parameters using standard protocols.

The results of these studies demonstrated that the highly transformed morphology of B104-1-1 cells was essentially unchanged after pE1Apr transfection but was markedly altered by pE1A transfection (FIG. 7). The B-E1A transfectants exhibit non-transformed flattened morphology and a contact-inhibited growth pattern (FIG. 7). Expression of E1A proteins in NIH3T3 cells did not significantly alter the monolayered morphology. The results indicated that E1A gene products could specifically reverse the transforming morphology of the neu-transformed cells.

DNA synthesis was also studied as a measure of cell growth, to determine whether the B-E1A transfectants were actively synthesizing DNA as compared to controls. These studies were conducted through the use of a [$^3$H]-thymidine incorporation assay. For these studies, cells were plated in ten replica into 96 well plates at a density of 9×10$^3$ cells/well and cultured in DMEM supplemented with 10% calf serum. [$^3$H]-thymidine (1 µCi) was added to each well at time points of 16, 40 and 64 h and continuously incubated at 37° C. for 2 h. Cells were then harvested and cellular DNA were bound to glass fiber filters. Radioactivities of individual samples were counted by Scintillation counter. Average cpm were calculated from ten replicate samples.

Figure 8A:
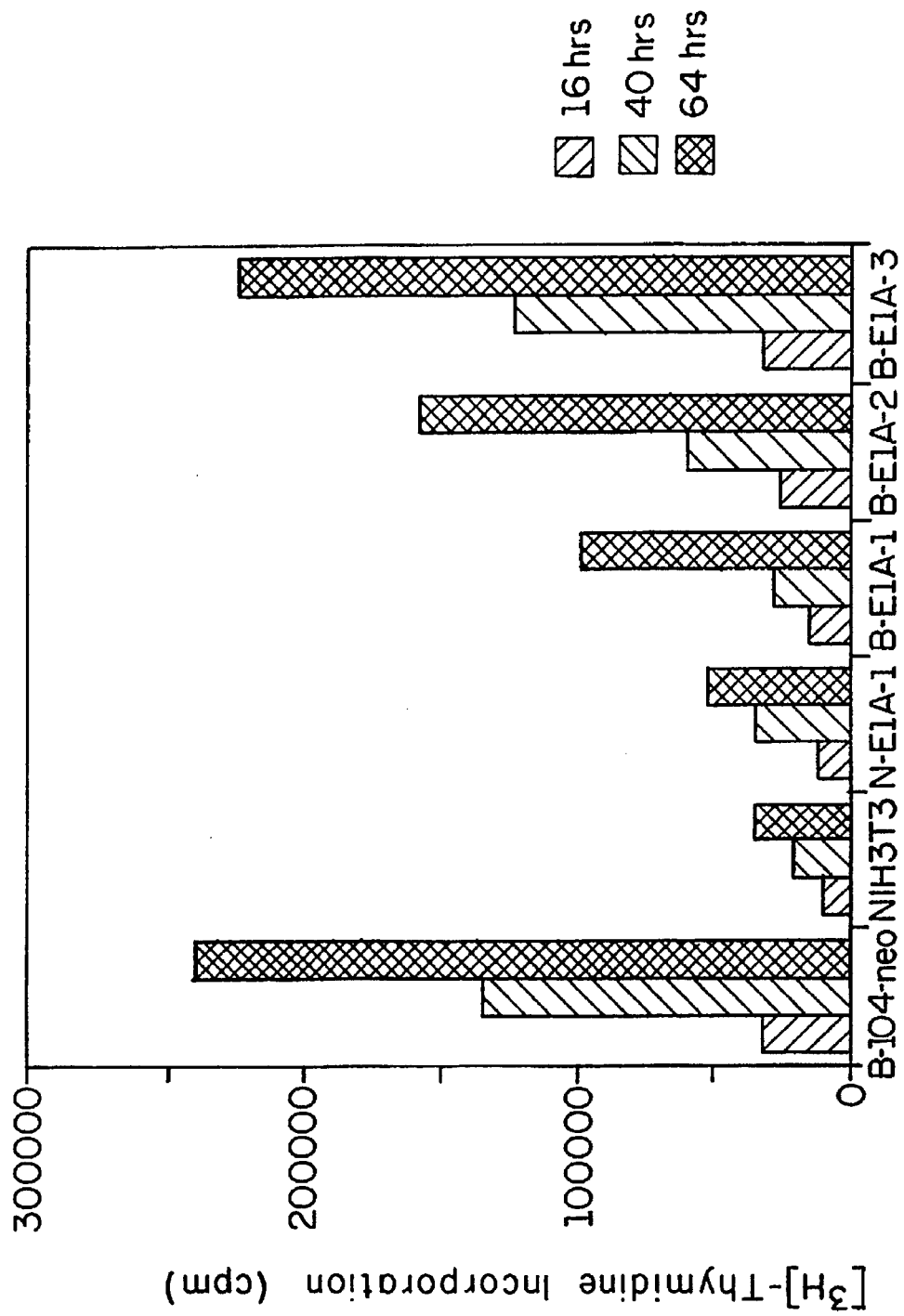

The rate of DNA synthesis, as indicated by [$^3$H]-thymidine incorporation, was different among the three B-E1A transfectants (FIG. 8a). B-E1A-1 and B-E1A-2 displayed a much lower DNA synthesis rate, which coincided with their slower cell growth rate compared to B104-1-1 cells. This E1A-induced decrease in [$^3$H]-thymidine incorporation was not as dramatic in the B-E1A-3 cell line possibly due to the lower level of the E1A proteins. These data suggested that E1A proteins can inhibit the effect of the neu oncogene on DNA synthesis and cell growth.

To test the influence of the E1A proteins on anchorage-independent growth, B104-1-1 cells and the B-E1A transfectants were assayed for their ability to grow in soft agar. The ability of B104-1- cells, B-E1A transfectants, NIH3T3 cells and N-E1A transfectant to grow in soft agarose was determined as described previously (Matin et al., 1990). Cells (1×10$^3$ cells/plate) were plated in a 24 well plate in DMEM containing 10% calf serum and 0.35% agarose (BRL, Gaithersburg, Md.) over a 0.7% agarose lower layer. The cells were incubated at 37° C. for 3 weeks and the plates were stained with p-iodonitrotetrazolium violet (1 mg/ml) for 24 h at 37° C. and colonies were counted.

Figure 8B:
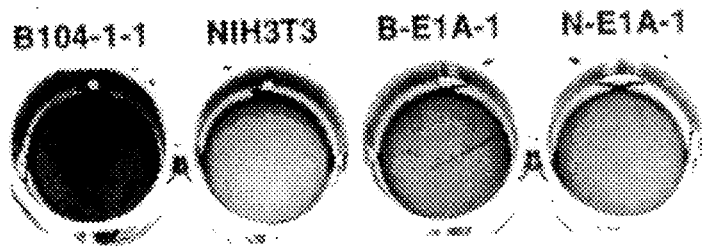

The results of the soft agar studies demonstrated that colony formation by the E1A transfectants were strikingly reduced compared to that of B104-1-1 and B-E1A pr transfectants (FIG. 8b). It is noteworthy that the colony formation by NIH3T3 and N-E1A-1 lines did not vary significantly.

The most stringent experimental test for neoplastic behavior is the ability of injected cells to form tumors in nude mice. Studies in nude mice were conducted because the examination of E1A repression of neu-mediated tumorigenicity in vivo was considered to be a critical test of E1A effectiveness. For conducting tumorigenicity studies, the B104-1-1 cells, B-E1A transfectants, NIH3T3 cells and N-E1A transfectant in log-phase growth were trypsinized and washed twice with phosphate buffered saline and centrifuged at 250×g. The viable cells were then counted, and $1 \times 10^5$ cells in 0.1 ml of phosphate buffered saline were injected subcutaneously into both the right and left flanks of 5 to 6-week old female homozygous nu/nu (nude) mice (Harlan Sprague Dawley Co.) under sterile conditions. Tumor formation was scored at indicated days as presence or absence of a visible tumor mass. Sixteen days after injection, tumor volumes were estimated as the product of three-dimensional caliper measurements (longest surface length and width and tumor thickness). The growth of tumors was monitored for a minimum of 16 days and maximum of 2 months.

When cells of the parental B104-1-1 line were injected subcutaneously in nude mice, solid tumors developed by 8 days after injection; however, the same quantity of the E1A transfectants did not form tumors in nude mice until 12–26 days after injection and in every case the tumors were much smaller than those from B104-1-1 cells (FIG. 9a).

Although the B-E1A-1 and B-E1A-2 transfectants contained comparable amounts of the E1A gene, the B-E1A-1 cells did not cause tumor development until a much later time. This is probably due to the lower level of neu gene in this line. On the other hand, although both of the B-E1A-2 and B-E1A-3 transfectants contained the same level of the neu gene as B104-1-1, the transforming suppression effect on B-E1A-3 was not as strong as on B-E1A-2. This was likely due to the lower level of the E1A gene in B-E1A-3. Typical results of E1A expression on neu oncogene induced tumorigenicity are shown in the photographs in FIGS. 9b and 11a. Evaluated 18 days after injection, animals injected with B104-1-1 cells were found to bear huge tumors, whereas those injected with B-E1A-2 transfected cells had considerably smaller tumor nodules. As expected, control animals injected with NIH3T3 cells showed no evidence of tumor formation.

Previous studies of Wilms' tumor cells and human prostate carcinoma DU145 cells demonstrated that reintroduction of chromosome 11 to Wilm's tumor cells or restoration of RB gene to DU145 cells suppressed tumor formation but did not alter the cell morphology, growth rate or colony-forming ability (Weissman et al., 1987; Bookstine et al., 1990). These data suggest that growth rate in culture and tumorigenicity in nude mice are separable phenomena. In the present study, the B-E1A-1 and B-E1A-2 cells exhibited slower growth rate and much weaker tumorgenic activity. However, suppression of tumorgenicity cannot entirely be explained by their slower growth rate and decreased [$^3$H]-thymidine incorporation. For example, the B-E1A-3 cells possessed similar [$^3$H]-thymidine incorporation and cell growth rate as B104-1-1 cells, while their tumorigenic activity was markedly suppressed as well. Taken together, these results clearly demonstrate that introduction of the E1A gene into B104-1-1 cells suppresses all the transforming properties of the neu-transformed cells.

EXAMPLE III

Suppression of Neu-Mediated Metastasis by E1A Gene Products

Additional studies were conducted using B-E1A transfectants of B104-1-1 to demonstrate that E1A products also suppress neu-mediated metastasis. These studies employed B-E1A transfectants (B-E1A-1 through B-E1A-5) as well as the negative and positive controls, NIH/3T3 and B104-1-1, respectively, in a cell motility, in vitro invasion and an experimental metastasis assay.

Figure 11B:
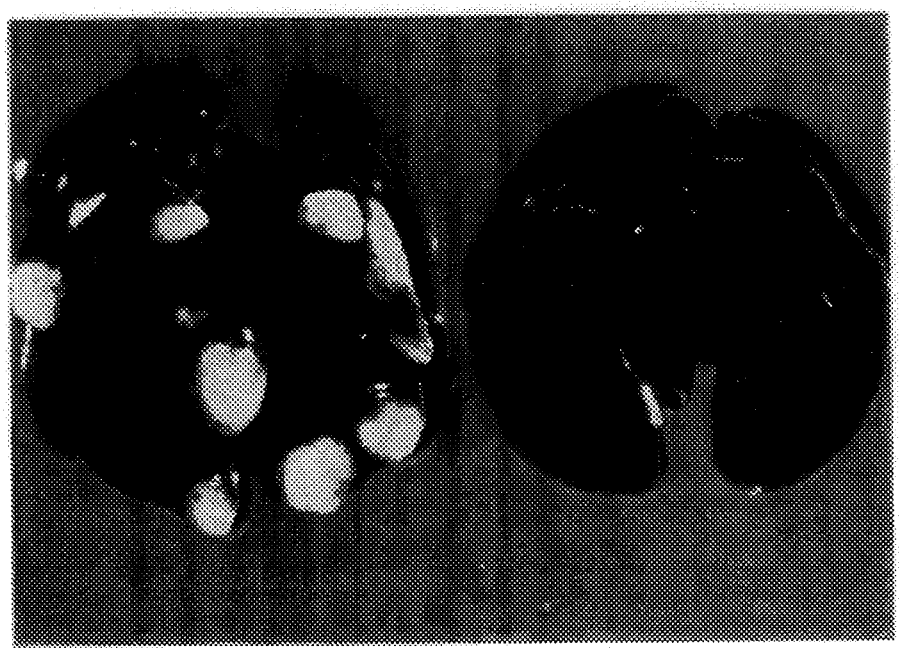

The metastasis studies were performed essentially as described by Wexler, 1966. Briefly, six-week-old pathogen-free female nude mice (Harland) were quarantined for 1 week and then used in the studies. Seven to ten mice/experimental group were inoculated with $1 \times 10^5$ cells/0.1 ml in PBS via the lateral tail vein at day 0. Each cell line was then assessed at two different passage numbers. Mice were sacrificed at 21 days following injection and the number of lung metastases were determined by infiltration with India ink. Only those lung nodules >1 mm in diameter were counted. On further examination, no extrapulmonary metastases were found. Representative photographs illustrating the gross appearance of the lungs from these animals are shown in FIG. 11b, whilst the quantitative data from these studies are detailed below in Table 1.

TABLE 1

EXPERIMENTAL METASTASIS ASSAY

| Cell Line | Transfected gene | Experimental metastasis | |
|---|---|---|---|
| | | Frequency | No. of lung nodules (mean ± SE) |
| NIH/3T3 | — | 0/9 | 0.0 ± 0.0 |
| B104-1-1 | neu | 9/9 | 10.9 ± 10.3 |
| N-E1A | E1A | 0/8 | 0.0 ± 0.0 |
| B-neo | neu + E1A | 7/7 | 9.5 ± 7.9 |
| B-E1A-1 | neu + E1A | 0/8 | 0.0 ± 0.0 |
| B-E1A-2 | neu + E1A | 3/9 | 0.8 ± 0.4 |
| B-E1A-3 | neu + E1A | 0/8 | 0.0 ± 0.0 |
| B-E1A-4 | neu + E1A | 1/7 | 0.1 ± 0.4 |
| B-E1A-5 | neu + E1A | 1/10 | 0.1 ± 0.4 |

The effectivenes of E1A at inhibiting neu-mediated metastasis is clearly illustrated in FIG. 11b. Furthermore, this single result was found to be representative of the entire study. None of the negative control mice, NIH/3T3 and E1A transfected NIH/3T3 (N-E1A), exhibited metastatic lung nodules. However, all of the positive controls (B104-1-1 and B-neo), exhibited metastatic nodules, at a mean frequency of about 10 nodules. In contrast, all of the experimental lines (B-E1A-1 through B-E1A-5) exhibited a reduced metastatic potential, with a frequency ranging from one to three (out of ten and nine, respectively), and a mean number of 0.1 to 0.8 nodules in those animals that were positive. Note that two of the experimental lines, B-E1A-1 and B-E1A-3, were totally free of metastases.

Figure 10A:
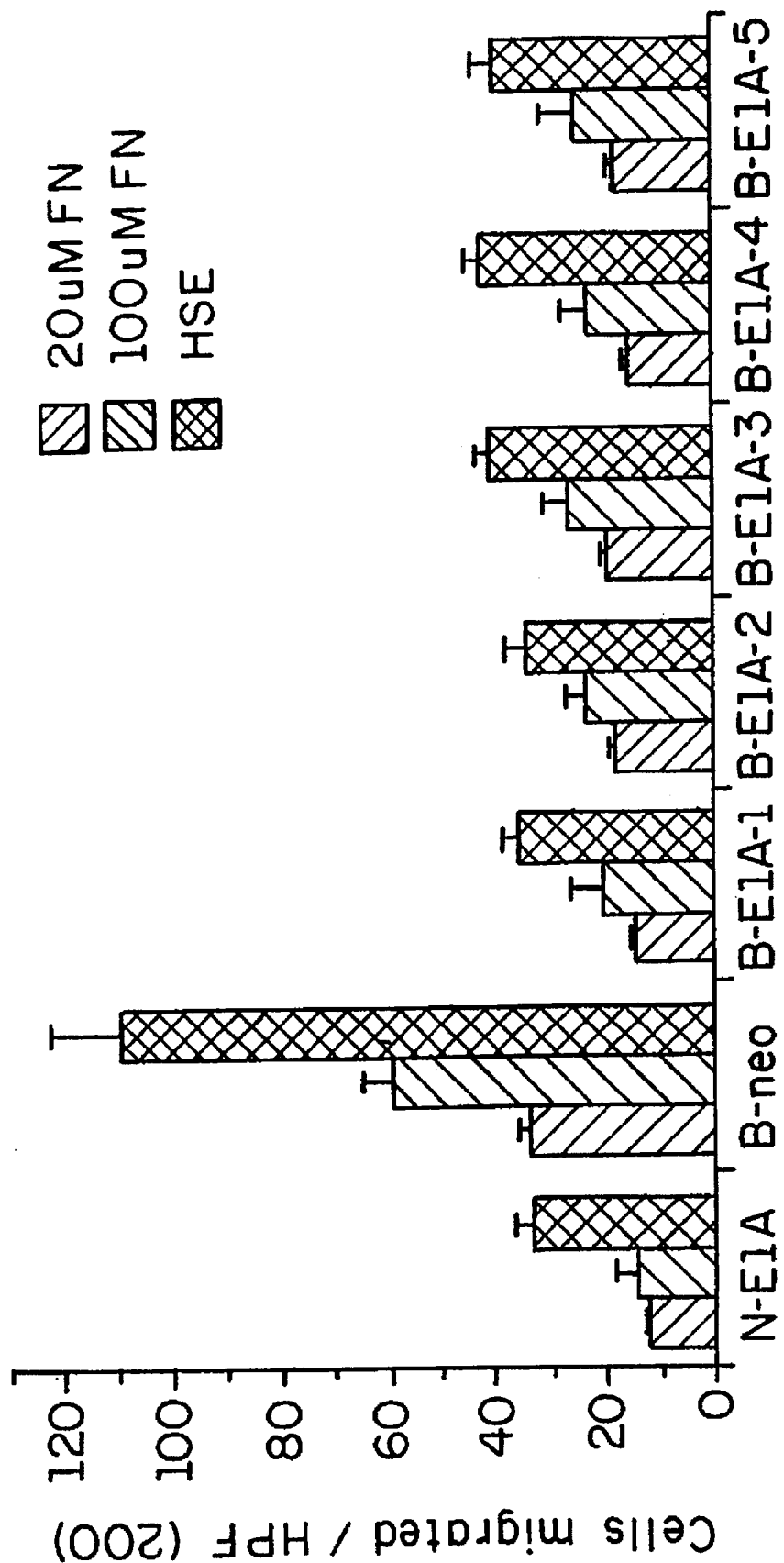

An increase in cell motility has been shown to correlate with a higher metastatic potential. Therefore, a motility assay, which measures the migration of the tested cell to a chemo-attractant, fibronectin or hepatic sinusoidal endothelial cell conditioned media, was performed. As shown in FIG. 10a, all of the B-E1A transfectants showed decreased migration rate to different chemoattractants than that of B-neo cell line, which are B104-1-1 cells transfected with neomycin-resistant (neo$^r$) gene alone. The N-E1A cells also had a low migration rate which is comparable to that of NIH3T3 cells.

Figure 10B:
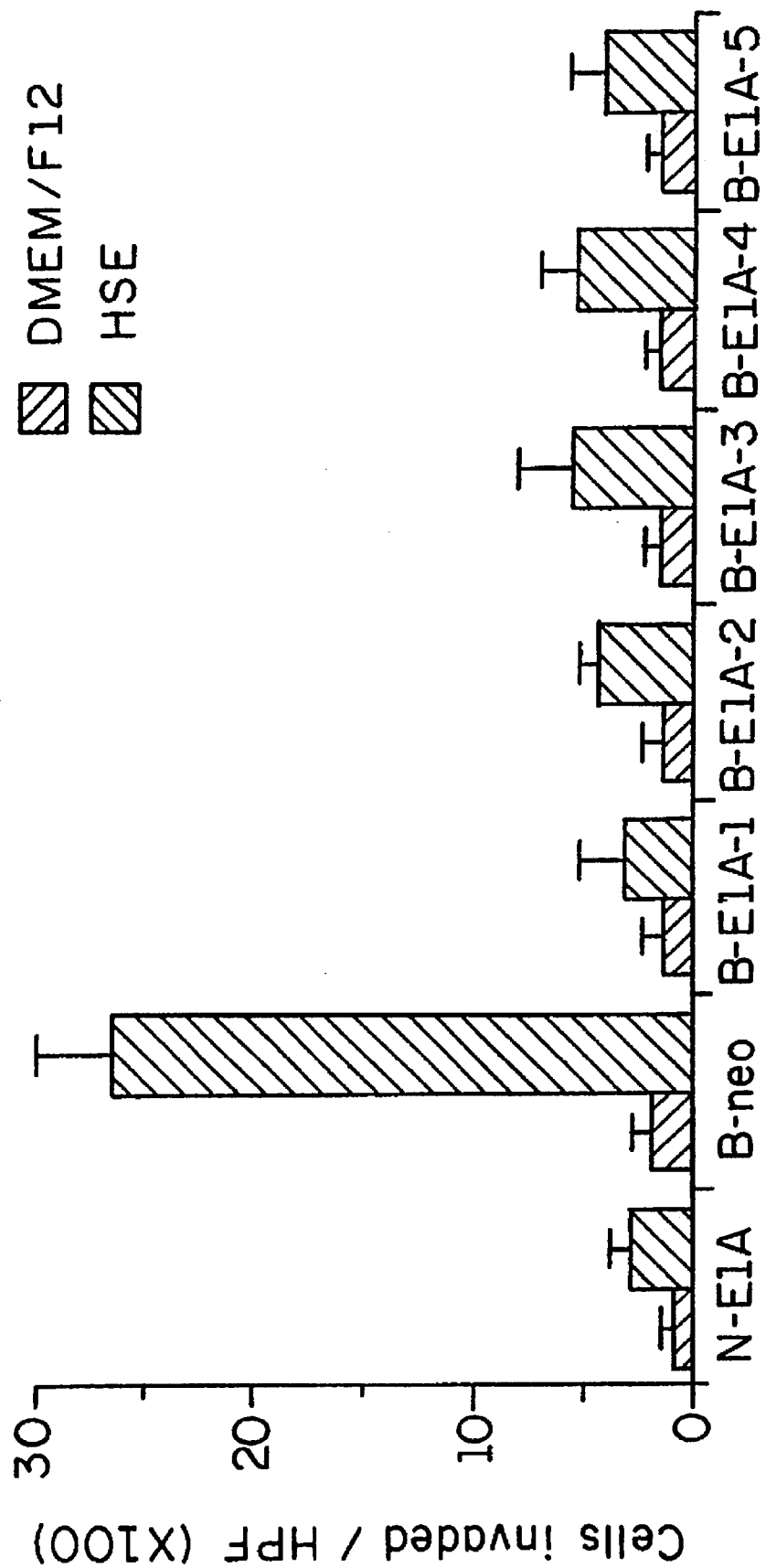
Figure 10C:
Figure 10D:
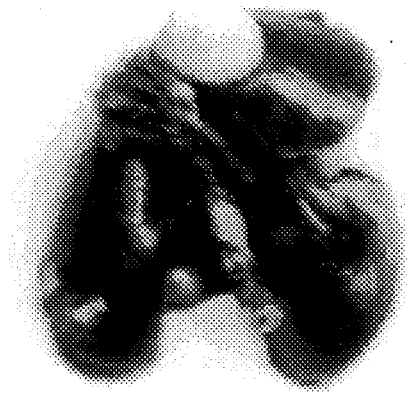
Figure 10E:
Figure 10F:

Another step in the metastatic process involves invasion of tissues and basement membranes. In vitro invasion assays also revealed significant differences between the B-neo cells and the B-E1A cell lines. B-neo cells demonstrated a high rate of invasion similar to that of B104-1-1 cells, while the B-E1A transfectants failed to invade the Matrigel. Injection of the B-neo cells and the five B-E1A cell lines into the tail vein of the nude mice showed dramatic differences in the frequencies and number of lung nodules (FIG. 10b and Table 1). Two of the five B-E1A transfectants did not give rise to any experimental metastatic tumors and the other three B-E1A lines had a very low incidence of experimental metastasis compared to that of B-neo cells (p >0.01). As expected, N-E1A cells were unable to produce any metastatic lung nodule. From these results, it is evident that E1A gene products can reduce the metastatic potential of neu-transformed 3T3 cells, possible by transcriptional repression of neu gene expression.

These results, typified by those shown in FIG. 11b, demonstrate that E1A gene products are able to suppress not only the tumorigenic and transformation events mediated by the neu gene (Example II), but are further able to suppress metastatic events that are neu mediated.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for or teach methodology, techniques and/or compositions employed herein.

Albini et al. (1987), *Cancer Res.*, 47:3239
Anderson et al. (1979), *Cell*, 16:63
Ausubel et al. (1987), *Current Protocols in Molecular Biology* (Greene/Wiley-Interscience, New York)
Bargmann et al. (1986), *Cell*, 45:649
Bargmann et al. (1986), *Nature*, 39:226
Berk et al. (1978), *Cell*, 14:695
Berk, A. J. (1986), *Ann. Rev. Genet.*, 20:45
Borrelli et al. (1984) *Nature*, 312:608
Campisi et al. (1983), *Cell*, 33:357
Chang et al. (1989), *J. Virol.*, 63:3479
Chen et al. (1988), *BioTechniques*, 6:632
Coussens et al. (1985), *Science*, 230:1132
Downward et al. (1984), *Nature* (London), 307:521
Figge et al. (1988), *Nature* (London), 334:109
Figge et al. (1988), *J. Virol.*, 62:1814
Gorman et al. (1982), *Mol. Cell. Biol.*, 2:1044
Haley et al. (1984), *Proc. Natl. Acad. Sci. USA*, 81:5734
Harlow et al. (1985), *J. Virol.*, 55:533).
Hearing et al. (1985), *Mol. Cell. Biol.*, 5:3214
Hen et al. (1985), *Science*, 230:1391
Houweling et al. (1980), *Virology*, 105:537
Hung et al. (1986), *Proc. Natl. Acad. Sci. USA*, 83:261.
Hung, M-C (1988), *The Cancer Bull.*, 40:300
Hung et al. (1989), *Proc. Natl. Acad. Sci. USA*, 86:2545
Kraus et al. (1987), *EMBO J.*, 6:605
Land et al. (1983), *Science*, 222:771
Lillie et al. (1989), *Nature* (London), 338:39
Liotta, L. A. (1989), in *Influence of Tumor Development on the Host*, vol. 7, pp 58–71, Kluwer Academic Publishers, Dordrecht.
Lupu et al. (1990), *Science*, 249:1552
Matin et al. (1989), *Oncogene*, 5:111
Mitchell et al. (1989), *Science*, 245:371
Moran et al. (1987), *Cell*, 48:177
Muller et al. (1982), *Nature* (London), 299:640
Pozzatti et al. (1988), *Mol. Cell. Biol.*, 8:2984
Repesh, L. A. (1989), *Invasion and Metastatsis*, 9:192
Ruley, H. E. (1985), *Nature*(London), 304:602
Robert et al. (1985), *Jrnl. Virol.*, 56:404
Sassone-Corsi et al. (1987), *Proc. Natl. Acad. Sci, USA*, 84:6430
Schechter et al. (1984), *Nature* (London), 312:513
Sebba et al. (1985), *Proc. Natl. Acad. Sci. USA*, 82:6497
Shih et al. (1981), *Nature* (London), 290:261
Slamon et al. (1987), *Science*, 235:177
Southern et al. (1982), *J. Mol. Appl. Genet.*, 1:327
Stein et al. (1987), *Mol. Cell. Biol.*, 7:1164
Tal et al. (1987), *Mol. Cell. Biol.*, 7:2597
Towbin et al. (1979), *Proc. Natl. Acad. Sci., USA*, 76:4350
Van Dam et al. (1989), *Oncogene*, 4:1207
Velcich et al. (1986), *Mol. Cell. Biol.*, 6:4019
Wallich et al. (1985), *Nature* (London), 315:301
Weinberg, R. A. (1985), *Science*, 230:770
Wexler, H. (1966), *Jrnl Natl. Cancer. Inst.*, 36:641
Whyte et al. (1988), *Nature* (London), 334,:124
Whyte et al. (1989), *Cell*, 56:67
Yamamoto et al. (1986), *Nature* (London), 319:230
Yarden et al. (1989), *Proc. Natl. Acad. Sci, USA*, 86:3179
Zhang et al. (1989), *Oncogene*, 4:985

We claim:

1. A method to suppress the growth of a neu oncogene-mediated tumor in a mammal, the method comprising introducing to said tumor a vector comprising a nucleic acid sequence encoding an adenoviral E1A gene product operatively linked to a promoter, wherein the production of the E1A gene product results in a decrease in the growth rate of said tumor.

2. The method of claim 1, wherein the vector comprises a plasmid vector.

3. The method of claim 1, wherein the vector comprises a viral vector.

4. The method of claim 3, wherein the vector comprises a retroviral vector.

5. The method of claim 1, wherein the E1A gene product comprises the E1A 12S gene product.

6. The method of claim 1, wherein the E1A gene product comprises the E1A 13S gene product.

7. The method of claim 1, wherein the E1A gene encodes the E1A 12S gene product.

8. The method of claim 1, wherein the E1A gene encodes the E1A 13S gene product.

* * * * *